(12) United States Patent
Cong et al.

(10) Patent No.: US 10,274,465 B2
(45) Date of Patent: Apr. 30, 2019

(54) CHROMATOGRAPHY OF POLYMERS

(75) Inventors: Rongjuan Cong, Lake Jackson, TX (US); Charles M. Cheatham, Lake Jackson, TX (US); Al Parrott, Lake Jackson, TX (US); Wallace W. Yau, Las Vegas, NV (US); Lonnie G. Hazlitt, Lake Jackson, TX (US); Zhe Zhou, Lake Jackson, TX (US); Alexander W. Degroot, Sugar Land, TX (US); Matthew D. Miller, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 261 days.

(21) Appl. No.: 14/119,403

(22) PCT Filed: Jun. 1, 2012

(86) PCT No.: PCT/US2012/040402
§ 371 (c)(1),
(2), (4) Date: Nov. 21, 2013

(87) PCT Pub. No.: WO2012/167035
PCT Pub. Date: Dec. 6, 2012

(65) Prior Publication Data
US 2014/0090453 A1 Apr. 3, 2014

Related U.S. Application Data

(60) Provisional application No. 61/493,121, filed on Jun. 3, 2011.

(51) Int. Cl.
*G01N 30/54* (2006.01)
*B01J 20/281* (2006.01)
(Continued)

(52) U.S. Cl.
CPC ............. *G01N 30/54* (2013.01); *B01D 15/34* (2013.01); *B01J 20/0285* (2013.01);
(Continued)

(58) Field of Classification Search
CPC .... B01J 15/34; B01J 20/0251; B01J 20/0259; B01J 20/0285; B01J 20/286;
(Continued)

(56) References Cited

U.S. PATENT DOCUMENTS 3,338,822 A     8/1967   Groszek et al.
4,160,728 A *   7/1979   Kirkland ................ B01D 15/34
                                                              210/656
(Continued)

FOREIGN PATENT DOCUMENTS

JP      2005054969 A      3/2005
SU          524127 A1     8/1976
(Continued)

OTHER PUBLICATIONS

Gavrilova, Journal of Chromatography Hydrocarbons, 1980 vol. 192 p. 323-330.*
(Continued)

*Primary Examiner* — Peter J Macchiarolo
*Assistant Examiner* — Nathaniel J Kolb

(57) ABSTRACT

The invention provides an apparatus for polymer chromatography, comprising at least one column that comprises a first stationary phase comprising one of the following: A) a material comprising at least one non-carbon atom, excluding glass or a metal, selected from molybdenum sulfide MoS2, tungsten sulfide WS2, silicon carbide SiC, boron nitride BN, or combinations thereof, or B) glass, or a metal, or combinations thereof, and a material comprising at least one non-carbon atom selected from molybdenum sulfide MoS2, tungsten sulfide WS2, silicon carbide SiC, boron nitride BN,
(Continued)

or combinations thereof. The invention also provides a method for polymer chromatography, comprising introducing a solution, comprising a polymer, into a liquid flowing through a first stationary phase, and wherein the first stationary phase comprises one of foregoing materials (A) or (B).

5 Claims, 6 Drawing Sheets

(51) Int. Cl.
    *B01D 15/34*     (2006.01)
    *B01J 20/02*     (2006.01)
    *B01J 20/286*     (2006.01)
    *B01J 20/32*     (2006.01)

(52) U.S. Cl.
    CPC ......... *G01N 30/482* (2013.01); *B01J 20/0251* (2013.01); *B01J 20/0259* (2013.01); *B01J 20/286* (2013.01); *B01J 20/3204* (2013.01); *B01J 20/3236* (2013.01); *B01J 2220/42* (2013.01)

(58) Field of Classification Search
    CPC ............... B01J 20/3204; B01J 20/3236; B01J 2220/42; G01N 30/02; G01N 30/2482; G01N 30/52; G01N 30/54; G01N 2030/025; G01N 2030/484
    See application file for complete search history.

(56) References Cited

U.S. PATENT DOCUMENTS

| | | | |
|---|---|---|---|
| 4,554,071 A * | 11/1985 | Ruijten | B01D 15/08 210/198.2 |
| 5,037,552 A | 8/1991 | Furuta et al. | |
| 5,098,576 A | 3/1992 | Cabrera et al. | |
| 5,272,236 A * | 12/1993 | Lai | B29C 47/0004 502/152 |
| 7,431,842 B2 * | 10/2008 | Haj-Ahmad | B01D 15/00 210/656 |
| 8,653,239 B2 | 2/2014 | Feckler | |
| 2001/0037674 A1 * | 11/2001 | Petro | B01D 15/08 73/61.52 |
| 2001/0051715 A1 * | 12/2001 | Taylor | B01D 15/366 536/25.4 |
| 2005/0191503 A1 | 9/2005 | Jones | |
| 2007/0237681 A1 * | 10/2007 | Boyle | B01J 20/28007 422/88 |
| 2008/0142445 A1 * | 6/2008 | Haj-Ahmad | B01D 15/00 210/660 |
| 2008/0307960 A1 | 12/2008 | Hendrickson et al. | |
| 2009/0173146 A1 * | 7/2009 | Pursch | G01N 30/30 73/61.52 |
| 2010/0003439 A1 * | 1/2010 | Michie, Jr. | C08L 23/0815 428/36.9 |
| 2010/0093964 A1 | 4/2010 | Van Damme et al. | |
| 2010/0278695 A1 | 11/2010 | Piper et al. | |
| 2011/0152499 A1 | 6/2011 | Winniford et al. | |

FOREIGN PATENT DOCUMENTS

| | | |
|---|---|---|
| SU | 610015 A1 | 6/1978 |
| WO | 1999/051980 A2 | 10/1999 |
| WO | 2011/084786 A1 | 7/2011 |
| WO | 2012/166861 A1 | 12/2012 |
| WO | 2003/098208 | 11/2013 |

OTHER PUBLICATIONS

EP14192505.7, Feb. 25, 2015, EP Search Report, 6 pages.
Albrecht, Macromolecules, 2007, vol. 40, p. 5545-5551.
Chitta, Journal of Chromatography A, 2010, vol. 1217, p. 7717-7722.
Cong, Macromolecular Symposia, 2012, vol. 312, p. 108-114.
Cong, Macromolecules, 2011, 44, pp. 3062-3072.
Findenegg, Carbon, 1987, vol. 25, No. 1, p. 119-128.
Gavrilova, Journal of Chromatography A, 1984, vol. 286, p. 49-55.
Ginzburg, Journal of Chromatography A, 2010, vol. 1217, p. 6867-6874.
Heinz, Polymer, 2005, vol. 46, p. 12040-12045.
Kern, Journal of Colloid and Interface Science, 1980, vol. 75, No. 2, 346-356.
Macko, J. Chrom. A, 2003, vol. 1002, p. 55-62.
Macko, Macromolecules, 2009, vol. 42, p. 6063-6067.
Macko, Polymer, 2009, vol. 50, p. 5443-5448.
Magonov, Journal of Macromolecular Science, Part B: Physics, 2006, vol. 45, p. 169-194.
Miller, Journal of Applied Polymer Science, 2010, vol. 123, No. 2, p. 1238-1244.
Roy, Macromolecules, 2010, vol. 43, p. 3710-3720.
Topalova, Journal of Chromatography Gas Chromatographic, 1986, vol. 364, p. 431-438.
Tracz, Polymer, 2006, vol. 47, p. 7251-7258.
Wang, Macromolecules, 2005, vol. 38, Is. 25, p. 10341-10345.
Yin, Surface and Interface Science, 2001, vol. 32, p. 248-252.
PCT/US2012/040402, International Search Report and Written Opinion of the International Searching Authority.
PCT/US2012/040402, International Preliminary Report on Patentability.
Gavrilova, Journal of Chromatography A, 1990, vol. 250, p. 41-46.
Monrabal, Macromolecular Symposia, 2012, vol. 312, No. 1, p. 115-129.
Coll, Applied Physics Express, 2008, vol. 1, p. 121701.1-121701.3.
Glass Bead 125um Specification, Jan. 2011.

* cited by examiner

Secondary Electron Micrographs of SiC Powder

➢ Flat regions on the SiC powder are observed on the order of 10 um²

CHROMATOGRAPHY OF POLYMERS

REFERENCE TO RELATED APPLICATIONS

The present application claims the benefit of U.S. Provisional Application No. 61/493,121, filed on Jun. 3, 2011, and incorporated herein by reference.

BACKGROUND OF THE INVENTION

The disclosed invention is in the field of liquid chromatography, especially in the field of high temperature liquid chromatography (HT-LC). Liquid chromatography is used to analyze, among other materials, polymers, with regard to molecular size, by Size Exclusion Chromatography (SEC), and, with regard to chemical composition, by High Performance Liquid Chromatography (HPLC). This disclosure relates to HT-LC of polymers, and, in particular, olefin-based polymers, with regard to chemical composition.

Olefin-based polymers (such as polymers and copolymers comprising polymerized ethylene monomer and/or propylene monomer) have long been analyzed with regard to chemical composition distribution by Temperature Rising Elution Fractionation (TREF), Crystallization Analysis Fractionation (CRYSTAF), and Crystallization Elution Fractionation (CEF). However, TREF, CRYSTAF, or CEF cannot be used to analyze amorphous polyolefin polymers. Furthermore, both TREF and CRYSTAF require a relatively long analysis time. Therefore, skilled persons turned to HPLC, in an attempt to reduce analysis time, and to expand the scope of analysis to amorphous polymers. Macko et al., apparently were the first to do so in 2003, by studying the retention of polyethylene standards on silica and zeolite stationary phases (J. Chrom. A, 1002 (2003) 55). Wang, et al., studied the retention of polyethylene and polypropylene by zeolites in 2005 (Macromolecules, 38 (2005) 10341). Heinz and Pasch used a silica stationary phase to analyze polyethylene—polypropylene blends by HPLC (Polymer 46 (2005) 12040). Albrecht, et al., used a silica stationary phase to analyze ethylene-vinyl acetate copolymers by HPLC (Macromolecules 2007, 40, 5545). Albrecht, et al., used a silica stationary phase to analyze ethylene-propylene copolymers by HPLC (Macromol. Symp. 2007, 257, 46).

Some chromatography separations using graphite are disclosed in the following references: Macko et al., *Separation of Propene/1-Alkene and Ethylene/1-Alkene Copolymers by High-Temperature Adsorption Liquid Chromatography*, Polymer 50 (2009), 5443-5448; Macko et al., *Separation of Linear Polyethylene from Isotactic, Atactic, and Syndiotactic Polypropylene by High-Temperature Adsorption Liquid Chromatography*, Macromolecules (2009), 42, 6063-6067; Roy et al., *Development of Comprehensive Two-Dimensional High Temperature Liquid Chromatography×Gel Permeation Chromatography for Characterization of Polyolefins*, Macromolecules (2010), 43, 3710-3720; and Ginzburg et al., *High-Temperature Two-dimensional Liquid Chromatography of Ethylene-Vinylacetate Copolymers*, Journal of Chromatography A, 1217 (2010), 6867-6874; Miller et al., *Separation of Polyolefins Based on Comonomer Content using High-Temperature Gradient Adsorption Liquid Chromatography with a Graphitic Carbon Column*, Journal of Applied Polymer Science, Vol. 123, No. 2, 1238-1244; Cong et al., *A New Technique for Characterizing Comonomer Distribution in Polyolefins: High Temperature Thermal Gradient Interaction Chromatography (HT-TGIC)*, Macromolecules, 2011, 44, 3062-3072; and Kern et al., Adsorption from Solution of Long-Chain Hydrocarbons onto Graphite: Surface Excess and Enthalpy of Displacement Isotherms, Journal of Colloid and Interface Science, Vol. 75, No. 2, 1980, 346-356. See also U.S. Publication No. 2010/0093964 (U.S. Pat. No. 8,076,147B2), and U.S. Publication No. 2011/0152499.

Additional chromatographies using graphite and/or polyethylene crystallization studies are disclosed in the following references: Chitta et al., *Elution Behavior of Polyethylene and Polypropylene Standards on Carbon Sorbents*, Journal of Chromatography A, 1217 (2010) 7717-7722; Findenegg et al., *Adsorption from Solution of Large Alkane and Related Molecules onto Graphitized Carbon*, Carbon Vol 25, No. 1, (1987), 119-128; and Yin et al., *Theoretical Study of the Effects of Intermolecular Interactions in Self-Assembled Long-Chain Alkanes Adsorbed on Graphite Surfaces*, Surface and Interface Analysis (2001), 32, 248-252, and Magonov, *Annealing and Recrystallization of Single Crystals of Polyethylene on Graphite: An Atomic Force Microscopy Study*, Journal of Macromolecular Science, Part B: Physics, 45, 2006, 169-194; and Tracz et al., *Unusual Crystallization of Polyethylene at Melt/Atomically Flat Interface: Lamellar Thickening Growth Under Normal Pressure*, Polymer, 47, 2006, 7251-7258.

A remaining problem for the HPLC analysis of polymers, and in particular, olefin-based polymers, is the limited separation efficiency obtained by the prior art methods (Cong et al., Macromolecular Symposia, 312, 108 (2012)). There remains a need for new chromatographic methods that provide improved separation efficiencies and reduced analysis times. These needs and others have been met by the following invention.

SUMMARY OF THE INVENTION

The invention provides an apparatus for polymer chromatography, comprising at least one column that comprises a first stationary phase comprising one of the following:

A) a material comprising at least one non-carbon atom, excluding glass or a metal, or B) glass, or a metal, or combinations thereof, and a material comprising at least one non-carbon atom.

The invention also provides a method for polymer chromatography, comprising introducing a solution, comprising a polymer, into a liquid flowing through a first stationary phase, and wherein the first stationary phase comprises one of the following:

A) a material comprising at least one non-carbon atom, excluding glass or a metal, or B) glass, or a metal, or combinations thereof, and a material comprising at least one non-carbon atom.

DETAILED DESCRIPTION

Figure 1:
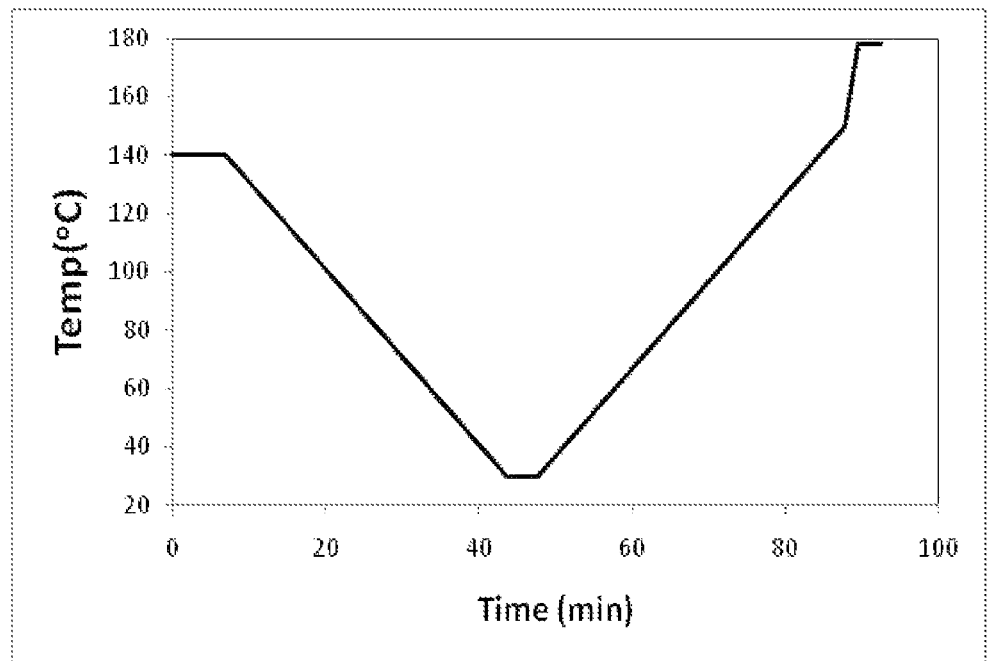
FIG. 1 depicts the "temperature versus time" profile for a typical HT-TGIC method.

As discussed above, the invention provides an apparatus for polymer chromatography, comprising at least one column that comprises a first stationary phase comprising one of the following:

A) a material comprising at least one non-carbon atom, excluding glass or a metal, or B) glass, or a metal, or combinations thereof, and a material comprising at least one non-carbon atom.

The invention also provides a method for polymer chromatography, comprising introducing a solution, comprising a polymer, into a liquid flowing through a first stationary phase, and wherein the first stationary phase comprises one of the following:

A) a material comprising at least one non-carbon atom, excluding glass or a metal, or B) glass, or a metal, or combinations thereof, and a material comprising at least one non-carbon atom.

An inventive apparatus may comprise a combination of two or more embodiments as described herein.

An inventive method may comprise a combination of two or more embodiments as described herein.

The embodiments described herein apply to both inventive aspects discussed above, unless otherwise noted.

In one embodiment, the first stationary phase comprises a material comprising at least one non-carbon atom, excluding glass or a metal.

In one embodiment, the first stationary phase comprises glass, or a metal, or combinations thereof, and a material comprising at least one non-carbon atom.

In one embodiment, the first stationary phase comprising at least one compound selected from the following: molybdenum sulfide ($MoS_2$), tungsten sulfide, silicon carbide, boron nitride, or combinations thereof.

In one embodiment, the first stationary phase comprising an atomically flat crystalline composition comprising at least two different atoms.

In one embodiment, the first stationary phase further comprises an inert filler, for example glass of a metal, or a combination thereof. In a further embodiment, the compound or the atomically flat crystalline composition is chemically bonded to the inert filler. In another embodiment, the compound or the atomically flat crystalline composition is coated onto the inert filler.

In one embodiment, the first stationary phase further comprises an inert filler, for example glass or a metal, or a combination thereof. In a further embodiment, the compound or the atomically flat crystalline composition is chemically bonded and/or coated to the inert filler.

In one embodiment, the first stationary phase further comprises an inert filler, for example glass or a metal, or a combination thereof. In a further embodiment, the compound is chemically bonded and/or coated to the inert filler.

In one embodiment, the first stationary phase further comprises an inert filler, for example glass or a metal, or a combination thereof. In a further embodiment, the atomically flat crystalline composition is chemically bonded and/or coated to the inert filler.

In one embodiment, the polymer is an olefin-based polymer. In a further embodiment, the olefin-based polymer is an ethylene-based polymer. In another embodiment, the olefin-based polymer is a propylene-based polymer.

In one embodiment, the atomically flat crystalline composition comprises at least one of the following: molybdenum sulfide ($MoS_2$); tungsten sulfide; silicon carbide; boron nitride, or combinations thereof.

In one embodiment, when a polyethylene homopolymer (density greater than 0.950 g/cc) is eluted through the "at least one column," its polymer fractions elute at higher elution peak temperatures, as compared to the elution temperatures of the same polyethylene homopolymer, eluted under the same chromatographic conditions, except that the stationary phase is formed only from glass ("1.5 refractive index" soda-lime glass, with a spherical percentage ≥90%, particle size was 125 μm±6%, available from MO-SCI Specialty Products). In a further embodiment, the polymer fractions, eluted through the at least one column, each elute at a elution peak temperature that is at least 3° C. higher than the peak elution temperature of the corresponding polymer fraction eluted through the glass. In a further embodiment, the polymer fractions, eluted through at least one column, each elute at an elution peak temperature that is at least 5° C. higher than the peak elution temperature of the corresponding polymer fraction eluted through the glass. In a further embodiment, the polymer fractions, eluted through the at least one column, each elute at an elution peak temperature that is at least 10° C. higher than the peak elution temperature of the corresponding polymer fraction eluted through the glass.

In one embodiment, when an ethylene-based polymer is eluted through the "at least one column," the resolution of its polymer fractions increases, as compared to the resolution of polymer fractions from the same ethylene-based polymer, eluted under the same chromatographic conditions, except that the stationary phase is formed only from glass ("1.5 refractive index" soda-lime glass, with a spherical percentage ≥90%, particle size was 125 μm±6%, available from MO-SCI Specialty Products). In a further embodiment, the ethylene-based polymer is a polyethylene homopolymer. In another embodiment, the ethylene-based polymer is an ethylene-based interpolymer, and further an ethylene-based copolymer.

In one embodiment, when an ethylene-based polymer is eluted through at least one column, the co-crystallization of its polymer fractions decreases, as compared to the co-crystallization of polymer fractions from the same ethylene-based polymer, eluted under the same chromatographic conditions, except that the stationary phase is formed only from glass ("1.5 refractive index" soda-lime glass, with a spherical percentage ≥90%, particle size was 125 μm±6%, available from MO-SCI Specialty Products). In a further embodiment, the ethylene-based polymer is a polyethylene homopolymer. In another embodiment, the ethylene-based polymer is an ethylene-based interpolymer, and further an ethylene-based copolymer.

In one embodiment, a polyethylene homopolymer (density greater than 0.950 g/cc) is eluted through the "at least one column" with an induced crystallization as compared to the polymer fractions from the same polyethylene homopolymer, eluted under the same chromatographic conditions, except that the stationary phase is formed only from glass ("1.5 refractive index" soda-lime glass, with a spherical percentage ≥90%, particle size was 125 μm±6%, available from MO-SCI Specialty Products).

In one embodiment, an ethylene-based polymer is eluted through the "at least one column" with an induced crystallization/and or enhanced interactions (for example, van der Waals interactions) as compared to the polymer fractions from the same ethylene-based polymer, eluted under the same chromatographic conditions, except that the stationary phase is formed only from glass ("1.5 refractive index" soda-lime glass, with a spherical percentage ≥90%, particle size was 125 μm±6%, available from MO-SCI Specialty Products). In a further embodiment, the ethylene-based polymer is a polyethylene homopolymer. In another embodiment, the ethylene-based polymer is an ethylene-based interpolymer, and further an ethylene-based copolymer.

In one embodiment, the apparatus further comprises a means to subject the first stationary phase to a temperature gradient. In a further embodiment, the temperature gradient (cooling or heating) is greater than, or equal to, 0.1° C. per minute, or greater than, or equal to, 1.0° C. per minute, or greater than, or equal to, 2.0° C. per minute.

A temperature gradient device (for example, a GC oven (Agilent Technologies), used in a CEF from PolymerChar) is an instrument that is used to thermally treat, or cool, a column (for example, a chromatography column) in a controlled manner. Other examples are Hewlett Packard GC ovens, and ATREF ovens (for example, see Gillespie et al., U.S. 2008/0166817A1).

In one embodiment, the apparatus further comprises a means to subject the first stationary phase to a solvent gradient.

A solvent gradient device (for example, a dual pump system with a mixer (Agilent Technologies) as available from PolymerChar) is an instrument that is used to mix two or more solvents in a controlled manner, and wherein the solvent mixture is used as an eluent in a column (for example, a chromatography column). Examples include a binary Shimadzu LC-20 AD pumps (see Roy et al, *Development of Comprehensive Two-Dimensional High Temperature Liquid Chromatography×Gel Permeation Chromatography for Characterization of Polyolefins*, Macromolecules 2010, 43, 3710-3720) and binary Agilent pumps from HT-LC instrument (PolymerChar).

In one embodiment, apparatus further comprises a means to subject the first stationary to a temperature gradient, and a means to subject the first stationary phase to a solvent gradient, for example, by using a combination of at least one oven and at least one pump as described above. In a further embodiment, the temperature gradient is greater than, or equal to, 0.1° C. per minute, or greater than, or equal to, 1.0° C. per minute, or greater than, or equal to, 2.0° C. per minute.

In one embodiment, the compound or the "atomically flat crystalline composition comprising at least two different atoms" is present in an amount greater than, or equal to, 10 weight percent, based on the weight of the first stationary phase.

In one embodiment, the compound is present in an amount greater than, or equal to, 10 weight percent, based on the weight of the first stationary phase.

In one embodiment, the "atomically flat crystalline composition comprising at least two different atoms" is present in an amount greater than, or equal to, 10 weight percent, based on the weight of the first stationary phase.

In one embodiment, the first stationary phase comprises a median particle size diameter, D50 from 3 to 250 μm.

In one embodiment, the apparatus further comprises a second stationary phase that is different from the first stationary phase. For example, the second stationary phase may differ from the first stationary phase in one or more features, such as, chemical composition, mean particle size, particle size distribution, pore size and/or pore size distribution.

In one embodiment, the apparatus further comprises a means to subject the second stationary phase to a temperature gradient, for example by a combination of the ovens and pumps in the PolymerChar apparatus described above. In a further embodiment, the temperature gradient is greater than, or equal to, 0.1° C. per minute, or greater than, or equal to, 1.0° C. per minute, or greater than, or equal to, 2.0° C. per minute.

A temperature gradient device (for example, a GC oven (Aglent Technologies), used in a CEF from PolymerChar) is an instrument that is used to thermally treat, or cool, a column (for example, a chromatography column) in a controlled manner. Examples include Hewlett Packard GC ovens, and ATREF ovens (for example, see Gillespie et al., U.S. 2008/0166817A1).

In one embodiment, the apparatus further comprises a means to subject the second stationary phase to a solvent gradient.

A solvent gradient device (for example, a dual pump system with a mixer (Agilent Technologies) as available from PolymerChar) is an instrument that is used to mix two or more solvents in a controlled manner, and wherein the solvent mixture is used as an eluent in a column (for example, a chromatography column). Examples include a binary Shimadzu LC-20 AD pumps (see Roy et al, *Development of Comprehensive Two-Dimensional High Temperature Liquid Chromatography×Gel Permeation Chromatography for Characterization of Polyolefins*, Macromolecules 2010, 43, 3710-3720) and binary Agilent pumps from HT-LC instrument (PolymerChar).

In one embodiment, the apparatus further comprises a means to subject the second stationary phase to both a temperature gradient and a solvent gradient, for example, by using a combination of at least one oven and at least one pump as described above. In a further embodiment, the temperature gradient is greater than, or equal to, 0.1° C. per minute, or greater than, or equal to, 1.0° C. per minute, or greater than, or equal to, 2.0° C. per minute.

In one embodiment, both the first and second stationary phases are subjected to a temperature gradient. In a further embodiment, the temperature gradient is greater than, or equal to, 0.1° C. per minute, or greater than, or equal to, 1.0° C. per minute, or greater than, or equal to, 2.0° C. per minute.

In one embodiment, both the first and second stationary phases are subjected to a solvent gradient.

In one embodiment, both the first and second stationary phases are subjected to both a temperature gradient and a solvent gradient, for example, by using a combination of at least one oven and at least one pump as described above. In a further embodiment, the temperature gradient is greater than, or equal to, 0.1° C. per minute, or greater than, or equal to, 1.0° C. per minute, or greater than, or equal to, 2.0° C. per minute.

In one embodiment, the first stationary phase is subject to a temperature gradient. In a further embodiment, the temperature gradient (cooling or heating) is greater than, or equal to, 0.1° C. per minute, or greater than, or equal to, 1.0° C. per minute, or greater than, or equal to, 2.0° C. per minute.

In one embodiment, first stationary phase is subjected to a solvent gradient.

In one embodiment, the first stationary phase is subject to both a temperature gradient and a solvent gradient, for example, by using a combination of at least one oven and at least one pump as described above. In a further embodiment, the temperature gradient is greater than, or equal to, 0.1° C. per minute, or greater than, or equal to, 1.0° C. per minute, or greater than, or equal to, 2.0° C. per minute.

In one embodiment, the first stationary phase comprises a median particle size diameter, D50 from 3 to 250 µm.

In one embodiment, the method further comprises fractionating the solution comprising the polymer into polymer fractions, and introducing the polymer fractions into a second stationary phase that is different from the first stationary phase. For example, the second stationary phase may differ from the first stationary phase in one or more features, such as chemical composition, mean particle size, particle size distribution, pore size and/or pore size distribution.

In one embodiment, the second stationary phase is subject to a temperature gradient. In a further embodiment, the temperature gradient is greater than, or equal to, 0.1° C. per minute, or greater than, or equal to, 1.0° C. per minute, or greater than, or equal to, 2.0° C. per minute.

In one embodiment, the second stationary phase is subject to a solvent gradient.

In one embodiment, the second stationary phase is subject to both a temperature gradient and a solvent gradient, for example, by using a combination of at least one oven and at least one pump as described above. In a further embodiment, the temperature gradient is greater than, or equal to, 0.1° C. per minute, or greater than, or equal to, 1.0° C. per minute, or greater than, or equal to, 2° C. per minute.

In one embodiment, both the first and second stationary phases are subjected to a temperature gradient. In a further embodiment, the temperature gradient is greater than, or equal to, 0.1° C. per minute, or greater than, or equal to, 1.0° C. per minute, or greater than, or equal to, 2.0° C. per minute.

In one embodiment, both the first and second stationary phases are subjected to a solvent gradient.

In one embodiment, both the first and second stationary phases are subjected to both a temperature gradient and a solvent gradient, for example, by using a combination of at least one oven and at least one pump as described above. In a further embodiment, the temperature gradient is greater than, or equal to, 0.1° C. per minute, or greater than, or equal to, 1.0° C. per minute, or greater than, or equal to, 2.0° C. per minute.

In one embodiment, the first and/or the second stationary phase(s) further comprise(s) at least one inert filler. Inert fillers include, but are not limited to, inorganic materials, such as, but not limited to, glass, stainless steel shot, and copper shot. As used herein, the term "inert" refers to a material that does not chemically react or physically adsorb polymers from the solution or eluent, each used in the chromatographic process.

In one embodiment, the first stationary phase further comprises at least one inert filler. Inert fillers include, but are not limited to, inorganic materials, such as, but not limited to, glass, stainless steel shot, and copper shot.

In one embodiment, the second stationary phase further comprises at least one inert filler. Inert fillers include, but are not limited to, inorganic materials, such as, but not limited to, glass, stainless steel shot, and copper shot.

In one embodiment, the first and the second stationary phases, independently, further comprise at least one inert filler. Inert fillers include, but are not limited to, inorganic materials, such as, but not limited to glass, stainless steel shot, and copper shot.

In one embodiment, the first stationary phase comprises less than, or equal to 50 weight percent inert filler, or less than, or equal to 30 weight percent inert filler, based on the sum weight of the first stationary phase. In one embodiment, inert filler is in the form of spheres. In a further embodiment, the spheres have a diameter from 2 to 250 microns, or from 5 to 125 microns, or from 7 to 50 microns.

In one embodiment, the inert filler is glass.

In one embodiment, the inert filler is stainless steel shot.

In one embodiment, the inert filler is copper shot.

In one embodiment, the first stationary phase comprises less than, or equal to 50 weight percent glass, or less than, or equal to 30 weight percent glass, based on the weight of the first stationary phase. In one embodiment, the glass is in the form of spheres. In a further embodiment, the spheres have a diameter from 2 to 250 microns, or from 5 to 125 microns, or from 7 to 50 microns.

In one embodiment, the second stationary phase comprises greater than, or equal to 50 weight percent inert filler, or greater than, or equal to 60 weight percent inert filler, based on the weight of the second stationary phase. In one embodiment, the at least one filler is in the form of spheres. In a further embodiment, the spheres have a diameter from 2 to 150 microns, or from 5 to 125 microns, or from 7 to 50 microns.

In one embodiment, the inert filler is glass.

In one embodiment, the inert filler is stainless steel shot.

In one embodiment, the inert filler is copper shot.

In one embodiment, the second stationary phase comprises greater than, or equal to 50 weight percent glass, or greater than, or equal to 60 weight percent glass, based on the weight of the second stationary phase. In one embodiment, the glass is in the form of spheres. In a further embodiment, the spheres have a diameter from 2 to 250 microns, or from 5 to 125 microns, or from 7 to 50 microns.

In one embodiment, the liquid flowing through the first stationary phase is a strong eluent. Examples of strong eluents include, but are not limited to, 1,2-dichlorobenzene, 1,2,4-trichlorobenzene, and tetrachloroethylene.

In one embodiment, the liquid flowing through the first stationary phase is a weak eluent. Examples of weak eluent include, but are not limited to, decanol, diphenyl ether, decane, and ethylene glycol monobutyl ether (EGMBE).

In one embodiment, the polymer has a concentration in the solution of greater than 0.1 milligrams polymer per milliliter of solution. In a further embodiment, the polymer is an olefin-based polymer.

An inventive method can be coupled, on or off line, with other analytical methods. For example, the effluent from an SEC column containing a copolymer of a selected molecular size can be analyzed by Temperature Rising Elution Fractionation (TREF), Crystallization Elution Fractionation (CEF) or Thermal Gradient Interactive Chromatography (TGIC) to determine the comonomer ratio of the selected molecular sizes. See also Roy et al., *Development of Comprehensive Two-Dimensional High Temperature Liquid Chromatography×Gel Permeation Chromatography for Characterization of Polyolefins*, Macromolecules (2010), 43, 3710-3720; Gillespie et al., "APPARATUS AND METHOD FOR POLYMER CHARACTERIZATION", US2008/0166817A1; each incorporated herein by references.

The Crystallization Elution Fractionation (CEF) technique relies mainly upon the ability of polymers to crystallize from a moving carrier upon reducing temperature (Monrabal, et al., "Crystallization elution fractionation. *A New Separation Process for Polyolefin Resins*, Macromol. Symp. 2007. 257, 71-79). The crystallization substrate is normally spherical glass beads, or stainless steel shot, or a mixed spherical glass beads with stainless steel shot, and is more or less inert with respect to physical interaction with the polymer in solution. A modification of the technique substitutes a more interactive substrate, for example, a carbon surface in a commercial column known as HYPERCARB, potentially possible packing materials of carbon nanotubes or silicon nanotubes for surface area and surface property, and does not rely upon the crystallizibility of the polymer from solution as the key driving force, but rather, on the adsorption to the carbon surface at a certain temperature. The new technique is known as Thermal Gradient Interaction Chromatography (TGIC). Both CEF and TGIC rely upon a thermal gradient to elute polymer.

The method of this disclosure could be scaled up to include large scale fractionations of many grams or many pounds of polymer, by scaling up the size of the apparatus and the column(s).

An inventive method may comprise a combination of two or more embodiments as described herein.

An inventive apparatus may comprise a combination of two or more embodiments as described herein.

The first stationary phase may comprise a combination of two or more embodiments as described herein.

The second stationary phase may comprise a combination of two or more embodiments as described herein.

First Stationary Phase

In one embodiment, first stationary phase comprising at least one compound selected from the following: molybdenum sulfide (MoS2), tungsten sulfide, silicon carbide, boron nitride, or combinations thereof.

In one embodiment, the first stationary phase comprising an atomically flat crystalline composition comprising at least two different atoms.

In one embodiment, the "first stationary phase" is a crystalline structure at a temperature range from −15° C. to 230° C.

In one embodiment, the "first stationary phase" is thermally stable at a temperature range from −15° C. to 230° C.

In one embodiment, the "first stationary phase" is chemically stable at a temperature range from −15° C. to 230° C.

In one embodiment, the "first stationary phase" is thermally and chemically stable at a temperature range from −15° C. to 230° C.

Chemically stable means that the stationary phase does not undergo chemical reaction with mobile phase or with polymer solution; and does not undergo thermal decomposition. Thermally stable describes a stationary phase that does not undergo substantial thermal expansion or contraction, which expansion or contraction causes the column bed to move or to generate voids, or which causes deterioration of the column performance in a relatively short period of time.

In one embodiment, the "first stationary phase" has a crystalline structure, as determined by X-ray diffraction.

In one embodiment, the first stationary phase comprises at least one of the following: silicon carbide; boron nitride, or combinations thereof.

In one embodiment, the "the first stationary phase" is silicon carbide.

In one embodiment, the "the first stationary phase" comprises any of the two elements: carbon, boron, sulfur or silicon or nitrogen. One example is white graphite.

In one embodiment, the "the first stationary phase" has a hydrophobic surface.

In one embodiment, the "the first stationary phase" is coated or chemically bonded onto another substrate to form a core-shell particle structure.

In one embodiment, the "the first stationary phase" has a hexagonal crystal structure.

In one embodiment, the "the first stationary phase" has a hexagonal sheet structure.

In one embodiment, the "the first stationary phase" increases the resolution of the polymer fractions, compared to glass beads.

In one embodiment, the "the first stationary phase" decreases the co-crystallization of the polymer fractions, compared to glass beads.

In one embodiment, the "the first stationary phase" enhances the affinity of the polymer fractions onto this phase, compared to the affinity of the polymer fractions on glass beads.

Atomic-height steps are a common feature of solid surfaces and they play important roles in many processes. Atomically flat surfaces are useful for many technical applications, and are typically defined as perfect, step-free surfaces. The theory describing the properties and characterization of such surfaces are known. See for example "Surface Roughening, Melting, and Faceting", E. H. Conrad, Progress in Surface Science, Vol. 39, Pergamon Press, 1992, pp 65-116. Efforts to synthetically prepare such surfaces have recently become of interest for instance in the electronics industry. See for example "Preparing arrays of large atomically flat regions on single crystal substrates," F. El Gabaly., N C. Bartelt, and A. K. Schmidt, J. Phys.: Condens. Matter, 21 (2009), 314019 (pp 1-7) and "Homoepitaxial 'Web Growth' of SiC to Terminate C-Axis Screw Dislocations and Enlarge Step-Free Surfaces," P. G. Neudeck, J. A. Powell, A. Trunek, D. Spry2, G. M. Beheim, E. Benavage, P. Abel, W. M. Vetter, and M. Dudley, Materials Science Forum Vols. 389-393, 2002, pp. 251-254, ©

2002 Trans Tech Publications, Switzerland. Such surfaces can also occur naturally or after cleaving the crystals, as in, for example, silicon carbide crystals.

In the present invention the term "atomically flat crystalline composition" as used herein, refers to a composition having easily identifiable surfaces (for example, the surfaces are identifiable using the scanning electron microscopy method discussed below) with an area of at least 10 μm², and wherein the surface is flat (i.e., free of any observable defect greater than about 10 nm) when examined using a scanning electron microscope, in a manner to be described below.

Experimental Method for the determination of "atomically flat crystalline composition"

Figure 9:
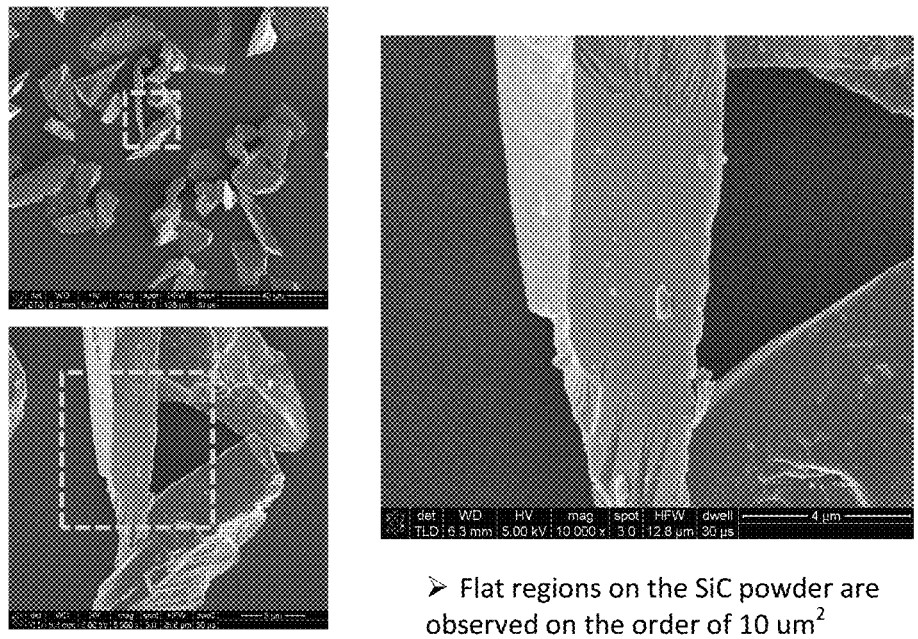
FIG. 9 illustrates the experimental method for the determination of "atomically flat crystalline composition"
Figure 10:
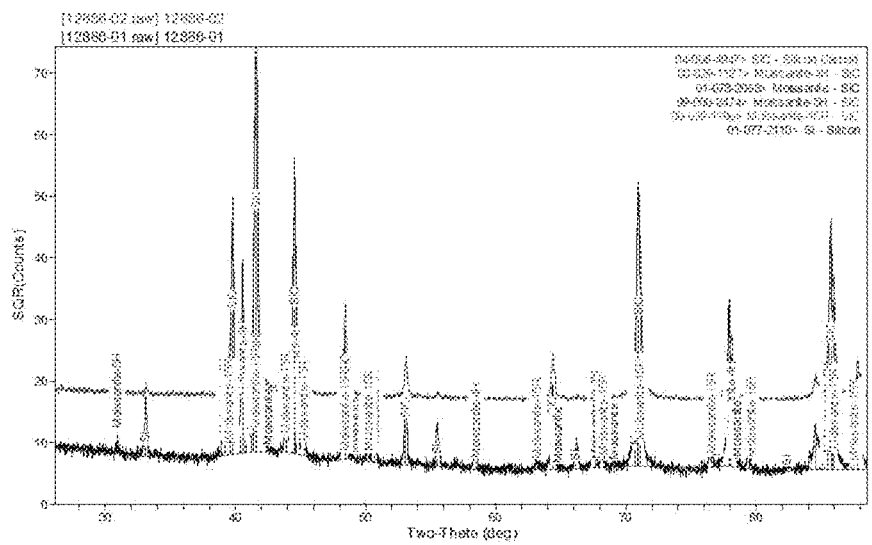
FIG. 10 illustrates the crystalline structures with XRD spectrum on the silicon carbide.
Figure 11:
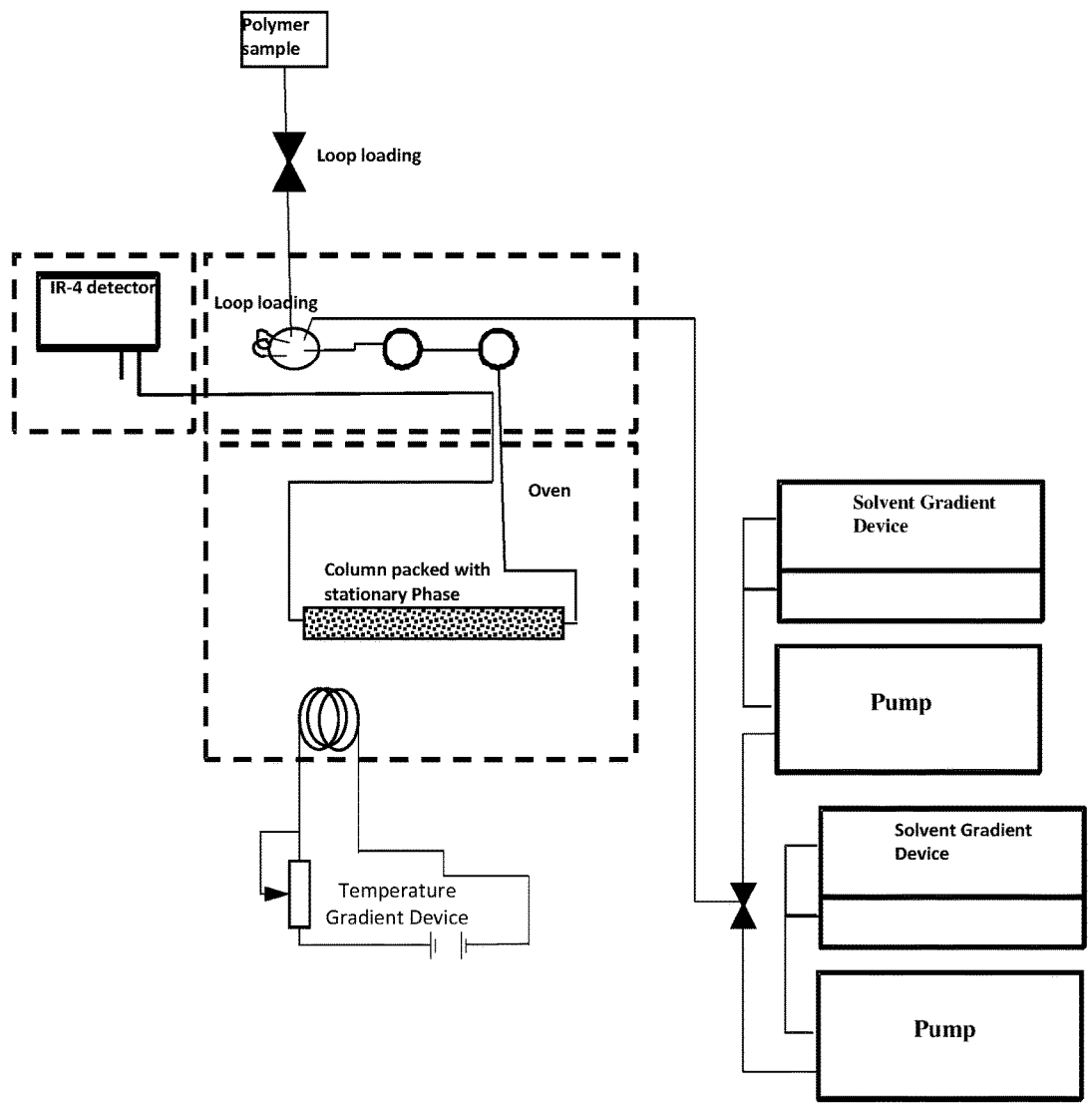
FIG. 11 depicts key components of an HT-TGIC apparatus.

Secondary electron images were collected, using an FEI NOVA NanoSEM 600 field emission scanning electron microscope (SEM). The SiC powder was distributed onto double sided tape on an aluminum "1" stub," and sputter coated using iridium. Imaging was done at about 6 mm working distance, using 5 kV accelerating voltage and spot size 3. The lower magnification images were acquired using an Everhart-Thornley (ETD) secondary electron detector, and the higher magnification images were acquired using a through lens detector (TLD). See FIG. 9.

Polymers

The following embodiments may apply to both the inventive SEC methods and the inventive SEC apparatus.

In one embodiment, the polymer is a nonpolar polymer, for example, polyethylene, polypropylene and polystyrene.

In one embodiment, the polymer is a polar polymer, for example, ethylene vinyl acetate.

In one embodiment, the polymer is an olefin-based polymer.

In one embodiment, the olefin-based polymer is an ethylene-based polymer.

In one embodiment, the olefin-based polymer is an ethylene/alpha-olefin interpolymer. In a further embodiment, the alpha-olefin is a C3-C10 alpha-olefin, and preferably selected from propylene, 1-butene, 1-hexene, and 1-octene.

In one embodiment, the olefin-based polymer is an ethylene/alpha-olefin copolymer.

In a further embodiment, the alpha-olefin is a C3-C10 alpha-olefin, and preferably selected from propylene, 1-butene, 1-hexene, and 1-octene.

In one embodiment, the olefin-based polymer is a copolymer of ethylene and an alpha-olefin. In a further embodiment, the alpha-olefin is 1-butene or 1-octene.

In one embodiment, the olefin-based polymer is a polyethylene homopolymer.

In one embodiment, the olefin-based polymer is a propylene-based polymer.

In one embodiment, the olefin-based polymer is a propylene/alpha-olefin interpolymer. In a further embodiment, the alpha-olefin is ethylene, or C4-C10 alpha-olefin, and preferably selected from ethylene, 1-butene, 1-hexene, and 1-octene.

In one embodiment, the olefin-based polymer is a propylene/alpha-olefin copolymer. In a further embodiment, the alpha-olefin is a C2, or C4-C10 alpha-olefin, and preferably selected from ethylene, 1-butene, 1-hexene, and 1-octene.

In one embodiment, the olefin-based polymer is a copolymer of propylene and an C4-C10 alpha-olefin, and preferably selected from 1-butene, 1-hexene, and 1-octene.

In one embodiment, the olefin-based polymer is a copolymer of propylene and ethylene.

In one embodiment, the olefin-based polymer is a polypropylene homopolymer.

In one embodiment, the olefin-based polymer has a density less than, or equal to, 0.97 g/cc; or less than, or equal to, 0.96 g/cc; or less than, or equal to, 0.95 g/cc (1 cc=1 cm³).

In one embodiment, the olefin-based polymer has a density less than, or equal to, 0.92 g/cc; or less than, or equal to, 0.90 g/cc; or less than, or equal to, 0.88 g/cc (1 cc=1 cm³).

In one embodiment, the olefin-based polymer has a density less than, or equal to, 0.89 g/cc; or less than, or equal to, 0.88 g/cc; or less than, or equal to, 0.87 g/cc (1 cc=1 cm³).

In one embodiment, the olefin-based polymer has a density greater than, or equal to, 0.83 g/cc; or greater than, or equal to, 0.84 g/cc; or greater than, or equal to, 0.85 g/cc (1 cc=1 cm³).

In one embodiment, the olefin-based polymer has a density from 0.83 g/cc to 0.97 g/cc, or from 0.84 g/cc to 0.95 g/cc, or from 0.85 g/cc to 0.93 g/cc (1 cc=1 cm³).

In one embodiment, the olefin-based polymer comprises from 1 mole percent to 49 mole percent of an alpha-olefin, as determined by $^{13}$C NMR. Preferred alpha-olefins are discussed above.

In one embodiment, the olefin-based polymer comprises from 2 mole percent to 29 mole percent of an alpha-olefin, as determined by $^{13}$C NMR. Preferred alpha-olefins are discussed above.

In one embodiment, the olefin-based polymer comprises from 5 mole percent to 9 mole percent of an alpha-olefin, as determined by $^{13}$C NMR. Preferred alpha-olefins are discussed above.

Olefin-based polymers include, but are not limited to, low density polyethylene (LDPE), high density polyethylene (HDPE), heterogeneously branched linear polymers (include Ziegler-Natta polymerized polymers, such as LLDPE, and include products such as DOWLEX Linear Low Density Polyethylene (LLDPE) available from The Dow Chemical Company), homogeneously branched substantially linear polymer (such as AFFINITY Polyolefin Plastomers and ENGAGE Polyolefin Elastomers, both available from The Dow Chemical Company) homogeneously branched linear polymers (such as EXACT Polymers available from ExxonMobil), and olefin multiblock copolymers (such as INFUSE Olefin Block Copolymers available from The Dow Chemical Company).

Olefin-based polymers also include polypropylene homopolymers, impact propylene based copolymers, and random propylene based copolymers.

Other polymers include, but are not limited to, ethylene/acrylic acid copolymers, ethylene/vinyl acetate copolymers and ethylene/styrene interpolymers, halogenated polymers, polymers containing maleic anhydride moieties.

A polymer may comprise a combination of two or more embodiments as described herein.

An olefin-based polymer may comprise a combination of two or more embodiments as described herein.

An ethylene-based polymer may comprise a combination of two or more embodiments as described herein.

A propylene-based polymer may comprise a combination of two or more embodiments as described herein.

Definitions

Unless stated to the contrary, implicit from the context, or customary in the art, all parts and percents are based on weight, and all test methods are current as of the filing date of this disclosure.

The term "polymer," as used herein, refers to a polymeric compound prepared by polymerizing monomers, whether of the same or a different type. The generic term polymer thus embraces the term homopolymer (employed to refer to polymers prepared from only one type of monomer, with the understanding that trace amounts of impurities can be incorporated into the polymer structure), and the term interpolymer as defined hereinafter.

The term "interpolymer," as used herein, refers to polymers prepared by the polymerization of at least two different types of monomers. The generic term interpolymer includes copolymers (employed to refer to polymers prepared from two different monomers), and polymers prepared from more than two different types of monomers.

The term "olefin-based polymer," as used herein, refers to a polymer that comprises a majority amount of polymerized olefin monomer, for example ethylene or propylene, (based on weight of the polymer) and, optionally, at least one comonomer.

The term "ethylene-based polymer," as used herein, refers to a polymer that comprises a majority amount of polymerized ethylene monomer (based on weight of the polymer) and, optionally, at least one comonomer.

The term "ethylene-based interpolymer," as used herein, refers to a interpolymer that comprises a majority amount of polymerized ethylene monomer (based on weight of the interpolymer) and at least one comonomer.

The term "ethylene-based copolymer," as used herein, refers to a copolymer that comprises a majority amount of polymerized ethylene monomer (based on weight of the copolymer) and one comonomer, as the only two monomer types.

The term "ethylene/α-olefin interpolymer," as used herein, refers to an interpolymer that comprises a majority amount of polymerized ethylene monomer (based on the weight of the interpolymer) and at least one α-olefin.

The term, "ethylene/α-olefin copolymer," as used herein, refers to a copolymer that comprises a majority amount of polymerized ethylene monomer (based on the weight of the copolymer), and an α-olefin, as the only two monomer types.

The term, "polyethylene homopolymer," as used herein, refers to a polymer that comprises only polymerized ethylene monomer.

The term "propylene-based polymer," as used herein, refers to a polymer that comprises a majority amount of polymerized propylene monomer (based on weight of the polymer) and, optionally, at least one comonomer.

The term "propylene-based interpolymer," as used herein, refers to a interpolymer that comprises a majority amount of polymerized propylene monomer (based on weight of the interpolymer) and at least one comonomer.

The term "propylene-based copolymer," as used herein, refers to a copolymer that comprises a majority amount of polymerized propylene monomer (based on weight of the copolymer) and one comonomer, as the only two monomer types.

The term "propylene/α-olefin interpolymer," as used herein, refers to an interpolymer that comprises a majority amount of polymerized propylene monomer (based on the weight of the interpolymer) and at least one α-olefin.

The term, "propylene/α-olefin copolymer," as used herein, refers to a copolymer that comprises a majority amount of polymerized propylene monomer (based on the weight of the copolymer), and an α-olefin, as the only two monomer types.

The term "composition," as used herein, includes a mixture of materials which comprise the composition, as well as reaction products and decomposition products formed from the materials of the composition.

The term "multidimensional chromatography," as used herein, refers to the coupling together of multiple separation mechanisms (for example, see J. C. Giddings (1990), Use of Multiple Dimensions in Analytical Separations, in Hernan Cortes Editor, *Multidimensional Chromatography: Techniques and Applications* (1st ed. pp. 1), New York, N.Y.: Marcel Dekker, Inc.).

The term "stationary phase," as used herein, refers to a material which exists in the fluid stream as a solid form in a chromatographic process.

Figure 7:
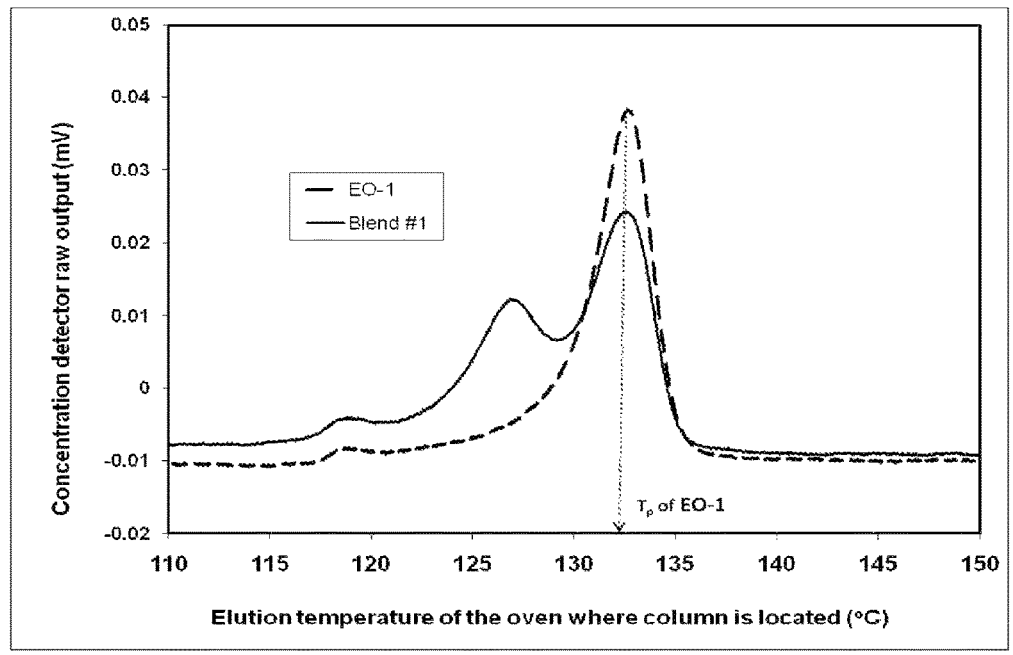
FIG. 7 depicts HT-TGIC chromatograms of the EO-1 polymer (dashed line) and Blend#1 (solid line), each obtained using an inventive molybdenum sulfide column (dimension 50 (L)×7.5 mm (ID)).

Elution peak temperature refers to temperature at maximum peak height (for example, see FIG. 7).

The terms "comprising," "including," "having," and their derivatives, are not intended to exclude the presence of any additional component, step or procedure, whether or not the same is specifically disclosed. In order to avoid any doubt, all compositions claimed through use of the term "comprising" may include any additional additive, adjuvant, or compound, whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed.

Test Methods

Density

Samples that are measured for density are prepared according to ASTM D 1928. Measurements are made within one hour of sample pressing using ASTM D792, Method B.

Melt Index

Melt index, MI or 12, is measured in accordance with ASTM D 1238, Condition 190° C./2.16 kg, and is reported in grams eluted per 10 minutes. The "I10" melt index is measured in accordance with ASTM D 1238, Condition 190° C./10 kg, and is reported in grams eluted per 10 minutes. For propylene-based polymers, the melt flow rate (MFR) is measured in accordance with ASTM D-1238, condition 230° C./2.16 kg.

Conventional GPC Mw Determination

To obtain Mw values, the chromatographic system consist of either a Polymer Laboratories Model PL-210 or a Polymer Laboratories Model PL-220. The column and carousel compartments are operated at 140° C. Three Polymer Laboratories, 10-μm Mixed-B columns are used with a solvent of 1,2,4-trichlorobenzene. The samples are prepared at a concentration of "0.1 g of polymer" in "50 mL of solvent." The solvent used to prepare the samples contain 200 ppm of BHT. Samples are prepared by agitating lightly for four hours at 160° C. The injection volume used is "100 microliters" and the flow rate is "1.0 mL/min"Calibration of the GPC column set is performed with twenty one narrow molecular weight distribution polystyrene standards purchased from Polymer Laboratories. The polystyrene standard peak molecular weights are converted to polyethylene molecular weights using Equation 1:

$$M\text{polyethylene} = A(M\text{polystyrene})^B \quad \text{(Eq. 1)},$$

where M is the molecular weight, A has a value of 0.4316 and B is equal to 1.0. A third order polynomial is determined to build the logarithmic molecular weight calibration as a function of elution volume. Polyethylene equivalent molecular weight calculations are performed using VIS-COTEK TriSEC software Version 3.0. The precision of the weight-average molecular weight Mw is excellent at <2.6%. See Jani et al., U.S. Pat. No. 6,469,103.

D50 (D10, D90)

The particle size distribution is measured with ACCU-SIZER 780 OPTICAL PARTICLE SIZER (Particle Size System, Florida, USA), and uses the principle of Single article Optical Sizing (SPOS) to count and size particles, one at a time, thus eliminating missed particles, and providing accurate particle size and count information. The illumination/detection system, in the sensor, is designed to provide a monotonic increase in pulse height with increasing particle diameter. The standard calibration curve is obtained by measuring a series of standard polystyrene latex samples from NIST Traceable Monodisperse Standards (Duke). The detailed procedure for calibration can be found in the operation menu provided by Particle Size System. A particle size distribution (PSD) is constructed by counting a large amount of particles (at least 55,000 particles). The sample is suspended in methanol (HPLC grade) (other suitable solvents include mineral oil or silicon oil) at low enough concentration, according to the operation procedure provided by Particle Size System. D50, D10 and D90 are calculated by the software of ACCUSIZER 780. Other solvents suitable include TCB (HPLC grade) and ODCB (HPLC grade). The D10=0.5×D50, and the D90=1.5×D50. The D50, is defined as the mean particle size, in diameter, where half of the particle population (number distribution) resides above, or equal to, this D50 value, and half the particle population (number distribution) resides below this D50 value.

X-Ray Diffraction

The crystalline structures can be examined with an X-ray diffractometer, such as a BRUKER D-8 ADVANCE θ-θ X-ray diffractometer, equipped with a cobalt sealed-tube source (wavelength=1.78897 Å for cobalt K-alpha 1 radiation) and a VANTEC-1 linear position sensitive detector. JADE X-ray software can be used for data analysis, and to confirm the crystalline structure is the same as reported in literature for the material.

Present crystalline phases in the samples were analyzed by powder X-ray diffraction. The XRD sample patterns were collected using a BRUKER D8 ADVANCE θ-θ difractctometer, equipped with a position sensitive detector (PSD: VANTEC-1 detector; PSD electronic window set at 8°) and a cobalt radiation source/X-ray tube (1.7899 Å). XRD spectrum were collected between 5 and 90° 2θ, at a step size of 0.017°, and 2 second/step with locked coupled scans. The "International Center for Diffraction Data (ICDD)" powder diffraction database files and the MDI Jade search/match software were used for phase identification.

EXPERIMENTAL

Solvents and Chemicals for Column Packing and TGIC Experiments

Ortho-dichlorobenzene (ODCB, 99% anhydrous grade) and 2,5-di-tert-butyl-4-methylphenol (BHT, catalogue number B1378-500G, batch number 098K0686) were purchased from Sigma-Aldrich. Silica gel 40 (particle size 0.2-0.5 mm, catalogue number 10181-3) was purchased from EMD. The silica gel was dried in a vacuum oven at 160° C. for about two hours before use. Eight hundred milligrams of BHT and 5.0 grams of silica gel were added to two liters of ODCB for high temperature thermal gradient interaction chromatography (TGIC). This "ODCB containing BHT and silica gel" is now refer to as "ODCB". This ODCB was sparged with dried nitrogen ($N_2$) for one hour before use. Methanol (HPLC grade, catalogue number A454-4) and 1,2,4-trichlorbenzene (TCB) were purchased from Fisher Scientific.

Packing Material

The comparative glass beads were the "1.5 refractive index" soda-lime glass, with a spherical percentage ≥90%. This glass was purchased from MO-SCI Specialty Products (4040 HyPoint North, Rolla, Mo. 65401 USA) with the part number of GL0191B6/125AW. The particle size was 125 μm±6% according to MO-SCI Specialty Products. The glass beads were acid washed by MO-SCI Specialty Products upon request.

Silicon carbide was purchased from Beta Diamond Products Inc (P.O. Box 2069 Yorba Linda, Calif. 92885, USA) with a particle size of 600 grit.

Boron nitride was purchased from MK Impex Corp (6382 Lisgar Drive, Mississauga, Ontario, L5N 6×1, Canada). The catalogue number was MH-hBN-500 with a lot#09/243. The average particle size was 5.0 μm according to the vendor.

Molybdenum sulfide ($MoS_2$) was purchased from Rose Mill Co. (W, Hartford, Conn., USA), and is sold as a technical grade with a particle size of 10-30 μm.

Tungsten sulfide ($WS_2$) was purchased from M K Impex Corp (6382 Lisgar Drive, Mississauga, Ontario, L5N 6×1, Canada; catalogue number is MK-WS2-50), and had an average particle size 5.0 μm (lot number 126/11).

Cast stainless steel shot was provided by VULKAN BLAST SHOT with Chronital 10, at a diameter of 0.05-0.2 mm, at mesh size of 170-100. Extensive cleaning and fractionation were performed before use as described below.

Cast stainless steel shot has various contaminants, such as, dust, paramagnetic particles, organic contaminants and metal oxides. The existence of magnetic materials may lead to a slow corrosion when in contact with ODCB, under elevated temperature during HT-TGIC analysis.

The detailed washing procedure was as follows.

1) A half a pound of stainless steel shot was placed into an eight ounce (8 oz) glass bottle with a 1.5 inch TEFLON magnetic stirring bar (Fisher Scientific).
2) The stainless steel shot was washed with detergent (Thermo Scientific, Catalogue #2503-12-001) and water extensively to get rid of dirt and magnetic particles (the magnetic stir bar attracted magnetic particles). The attracted magnet particles were removed from magnetic stirring bar by wiping with a paper towel.
3) Step (3) was repeated several times until the water appeared clear and colorless, and no magnetic particles appeared to stick on magnetic stirring bar.
4) The stainless steel shot was further washed with acetone to get rid of organic contaminants. This step was repeated several times, until the acetone appeared clear and colorless.
5) The shot was rinsed with de-ionized water to get rid of residual acetone.
6) A "1% nitric acid solution" was added to cover the stainless steel shot. The mixture was stirred with a glass rod for five minutes, and kept under fume hood for 30 minutes with occasional stirring. The nitric acid solution was carefully decanted. The shot was rinsed several times with deionized water, until the water appeared clear and colorless.
7) Step (7) was repeated several times, or until the nitric acid solution appeared clear and almost colorless. It is impossible to get a colorless nitric solution. The shot contains some metal elements which are chemically active enough to be dissolved in 1% nitric acid.

Dry the shot under vacuum oven at 60° C., under N$_2$, to minimize possible oxidation of fresh surface of the shots.

After this cleaning procedure, the shots showed the typical luster of metal. Stainless steel shots were fractionated by using metal sieves with a desired mesh size. The particles with sizes from 125 μm to 250 μm were collected for packing the column.

Hardware for Packing Columns

Stainless column, frit, end fitting of the column and solution distributors were obtained from Agilent Technologies (previously PolymerLab Inc.) as the Gel Permeation Chromatography (GPC) (or Size exclusion chromatography (SEC)) column (dimension 300×7.5 mm) and guard column (dimension 50×7.5 mm) The original packing material inside the GPC column and guard column were emptied. The columns were cleaned with acetone, and dried under nitrogen (N$_2$) before being packed with the substrates specified above.

A Waters 1500 Liquid Chromatography Pump was used for the slurry packing method. TCB (1,2,4-trichlorobenzene) was the slurry medium. A slurry packing reservoir was constructed of "25.4 mm diameter" stainless steel tubing with Valco end fittings. The reservoir was "100 mm" in length. An adaptor to connect the packing reservoir to the empty analytical column was custom made at Superior Fabrication & Maintenance, Inc (Freeport, Tex., USA) by welding and drilling out end fittings and tubing to give a conveniently threaded system.

Methodologies for Packing Columns

The columns for use in high temperature thermal gradient interaction chromatography (HT-TGIC, or simply TGIC) include the following.

Packed columns that exhibit good mass transfer properties including low back pressure at standard operating conditions of flow and temperature, low sensitivity to shock from abruptly changing conditions, and lack of channels and void spaces.

Packed columns which are long enough to permit studies of effect of dynamic cooling on component resolution. The dynamic cooling is a process of using a slow flow during cooling process to further enhance HT-TGIC separation (Cong et al., Macromolecules, 2011, 44(8), 3062-3072).

Two methodologies of preparing columns are used: (1) dry packing by using the tap-and-fill method, in which the added material is settled by tapping the column or using an electric vibrating tool; and (2) slurry packing method, which uses a suspension or slurry of the substrate where the slurry is pumped into the column under flowing conditions (Striegel, Yau, et al., *Modern Sice Exclusion Liquid Chromatography*, Wiley, the 2$^{nd}$ edition, Chapter 6), For the simple tap-and-fill method, the column is suspended vertically. Substrate is added in small increments through a funnel, while the column being tapped or vibrated to settle the substrate. When the substrate is level with the end of the column, the end fitting is added, and the column is tightened. It is a standard practice to condition the columns prior to use, and to inspect the bed for settling or voids. If voids are found, more packing is added to level the end of the column.

For slurry packing method, in order to remove small particles, and to produce the slurry suspension, a sedimentation process is used. Because the bulk density of various kinds of substrates can vary considerably, the mass of substrate used is generally from 20 to 50 grams. The solid substrate is placed in a 100 or a 250 mL glass graduated cylinder, ODCB is added to the top mark of the cylinder. The mixture is stirred with a glass rod, and allowed to stand for five minutes. The top liquid layer with suspended fine particles, usually about 20-30 mL, is decanted and discarded. This process is repeated several times until the presence of fines in the decantate becomes visibly decreased. The remaining slurry of the substrate in ODCB is then poured into the packing reservoir. The reservoir and column with end fitting is then assembled, and connected to the Waters pump. TCB is pumped upward, at a flow of 3 mL/min, through the reservoir until air is displaced from the column. The flow is momentarily stopped, the column and reservoir is then inverted to a down-flow position. TCB is pumped at 3-5 mL/min through the column for at least twenty minutes, or until the system pressure reaches 2500 PSIG. The column is disconnected from the packing reservoir, and any excess packing at the end of the column is removed with a flat blade scraper to provide an even level with the end of the tubing. The end fitting is tightened into place, and the column is ready for conditioning.

Column Conditioning

The newly packed column is installed in the TGIC chromatography, and flow is established at 0.1 mL/min at room temperature. Depending on the material and how efficiently it is packed, the back pressure at this point is usually 2-10 Bar. The flow is increased in steps of 0.1 mL/min, allowing the pressure to stabilize between each increase, up to either 0.7 or 1.0 mL/min. The goal is to have the back pressure below 120 Bar, mainly to accommodate equipment limitations in polymer chromatography. If the pressure is acceptable at this point, the column temperature is increased to 60° C., and then a linear temperature ramp is used to heat the column, under flow, to 175° C. at 10° C./min. This final temperature is held for 20 minutes, and then the column is cooled at 10° C./min to 100° C., and pronounced ready for testing.

In summary, Table 1 shows the column information with various types of substrate and column dimension. The dimension is described as the length in millimeter followed by internal diameter in millimeter.

TABLE 1

| Column Information | | |
| --- | --- | --- |
| Column Description | Substrate | Packing method |
| Inventive silicon carbide column (dimension 300 × 7.5 mm) | Silicon carbide | Slurry packing |
| Comparative glass bead column (dimension 300 × 7.5 mm) | Glass bead 125 μm | Dry packing |
| Comparative Stainless shot column (dimension 300 × 7.5 mm) | Stainless shot column (125 μm to 250 μm) | Dry packing |
| Inventive molybdenum sulfide column (dimension 50 × 7.5 mm) | Molybdenum sulfide | Slurry packing |

TABLE 1-continued

Column Information

| Column Description | Substrate | Packing method |
|---|---|---|
| Comparative glass bead column (dimension 50 × 7.5 mm) | Glass bead 125 μm | Dry packing |
| Inventive mixed tungsten sulfide/glass column (dimension 50 × 7.5 mm) | Tungsten sulfide/glass bead mixed at 1:2 (wt:wt) | Slurry packing |
| Comparative glass bead column (dimension 50 × 7.5 mm) | Glass bead 125 μm | Dry packing |
| Inventive boron nitride column (50 × 7.5 mm) | Boron nitride | Slurry packing |
| Comparative glass bead column (50 × 7.5 mm) | Glass bead 125 μm | Dry packing |
| Inventive silicon carbide column (dimension 300 × 7.5 mm) | Silicon carbide | Slurry packing |
| Comparative HYPERCARB column (100 × 4.6 mm) | Graphite | Purchased from Fisher Scientific. Product N# 35005-104646, lot PGC416) |

Instrument for HT-TGIC

The "TGIC" was done with a commercial CEF equipped with an infrared detector IR-4 (PolymerChAR, Spain).

HT-TGIC experiment consisted of the four steps, as discussed in the following reference (see also Cong et al., Macromolecules, 2011, 44 (8), 3062-3072): (1) sample dissolution, (2) sample solution loaded onto a column, (3) cooling process where polymer fractions are anchored onto the substrate of column, and (4) elution process where the concentration of polymer fractions are measured.

Since the HT-TGIC experiments were conducted on a CEF instrument, which separated polymer based on crystallization in CEF, the "crystallization" used in CEF instrument method in CEF analysis, corresponded to the "cooling process" in HT-TGIC methodology. The temperature of the main oven (where the column/columns is/are located) versus time (which is the time elapsed since polymer solution being loaded, anchored and then eluted onto column), or the "column temperature versus time" profile, is shown in FIG. 1. The experimental parameters are listed in Table 2. For simplicity, "TGIC 140° C._30° C._150° C._3° C./min_3° C./min 0.15 mL/min_1.0 mL/min" represents the following experimental conditions for the TGIC run "Stabilization Temperature (° C.)_Final Temperature during Cooling Process (° C.)_Final Temperature during Elution Process (° C.)_Cooling Rate during Cooling Process (° C./min)_ Heating Rate during Elution Process (° C./min)_Flow Rate during Cooling Process (mL/min)_Flow Rate during Elution Process (mL/min)" (see also Cong et al., Macromolecules, 2011, 44 (8), 3062-3072)).

TABLE 2

Experimental Parameters for HT-TGIC using Commercial CEF Instrument

| Temperature profile | | Column loading and vial filling | |
|---|---|---|---|
| Stabilization Temperature | 140° C. | Column Load Volume | 0.2 mL |
| Stabilization Rate | 10° C./min | Solvent pick up flow rate | 25 ml/min |
| Stabilization Time (Pre) | 5 min | Vial filling flow rate | 5 ml/min |
| Stabilization Time (Post) | 2 min | | |
| Crystallization Temperature | 30° C. | Loop Loading and filter cleaning | |
| Crystallization Rate | 3° C./min | Sample pick up flow rate | 2 ml/min |
| Crystallization Time | 2 min | Sample pick up volume | 2 ml |
| SF Time | 2 min | Load Loop Flow Rate | 1.25 mL/min |
| Elution Temperature | 150° C. | Load Loop Volume | 1.2 mL |
| Elution Rate | 3° C./min | Clean Line Flow Rate | 1.25 mL/min |
| Cleaning Temperature | 178° C. | Clean Line Volume | 4 mL |
| Cleaning Rate | 15° C./min | Clean Filter Flow Rate | 4 mL/min |
| Cleaning Time | 3 min | Clean Filter Volume | 5 mL |
| | | Cleaning Transfer Line Flow Rate | 5 mL/min |
| Temperature Zones | | Cleaning Transfer Line Volume | 2.00 ml |
| Top Oven Temperature | 150° C. | | |
| Transfer Line Temp | 150° C. | Pump flow | |
| Needle Temp | 150° C. | Pump Stabilization Time | 15 s |
| | | Cleaning Column Pump Flow | 1 mL/min |

TABLE 2-continued

Experimental Parameters for HT-TGIC using Commercial CEF Instrument

| Temperature profile | | Column loading and vial filling | |
|---|---|---|---|
| Dissolution | | Crystallization Pump Flow | 0.15 mL/min |
| Dissolution Temperature | 160 C. | Elution Pump Flow | 1 mL/min |
| Dissolution Stirring | 2 | Load Column Pump Flow | 0.3 mL/min |
| Dissolution time | 2 hours | | |

The main oven (where the column(s) is/are located) temperature profile is shown in FIG. 1. These experimental parameters are used to generate chromatograms of EO-1 and EO-6 for the comparative glass bead column (dimension 300×7 5 mm) and the inventive silicon carbide column (dimension 300×7.5 mm)

Polymer Samples for HT-TGIC

A homopolymer polyethylene (EO-1) (density of 0.956 g/cm$^3$, melt index ($I_2$) of 1.0, a melt index ratio ($I_{10}/I_2$) of 6.7, a weight average molecular weight (Mw) of 115,000 Daltons, and a polydispersity (Mw/Mn) as 2.6), and ethylene-octene copolymers are listed in Table 3.

TABLE 3

Characterization Data for EO-1 to EO-7

| Sample ID | Catalyst/ Targets* | Density | Melting index I2 | I10/I2 | Mw measured by conventional GPC | Octene content, mol % |
|---|---|---|---|---|---|---|
| EO-1 | Constrained geometry catalyst | 0.957 | 1.0 | 6.7 | 115000 | 0.00 |
| EO-2 | Constrained geometry catalyst | 0.952 | 63.0 | N/A | 37500 | 0.49 |
| EO-3 | Constrained geometry catalyst | 0.924 | 1.0 | 6.4 | 104500 | 1.33 |
| EO-4 | Constrained geometry catalyst | 0.914 | 0.9 | 6.3 | 103800 | 2.54 |
| EO-5 | Constrained geometry catalyst | 0.904 | 1.0 | 6.4 | 102900 | 3.99 |
| EO-6 | Constrained geometry catalyst | 0.865 | 1.0 | 6.9 | 123400 | 13.88 |
| EO-7 | Constrained geometry catalyst | 0.957 | 0.95 | 6.7 | 104200 | 0.00 |

*See a) Metallocene-based polyolefins Volumes One and Two, edited by John Scheirs and Walter Kaminsky, Wiley series in Polymer Science, John Wiley & Sons, Ltd., (2000); and b) Innovations in Industrial and Engineering Chemistry - A Century of Achievements and Prospects for the New Millennium, ACS Symposium Series 1000, edited by William H. Flank, Martin A. Abraham, and Michael A. Matthews, American Chemical Society Copyright 2009; and c) History of Polyolefins, Edited by Raymond B. Seymour and Tai Cheng, D. Reidel Publishing Company, 1986.

Sample Preparation for HT-TGIC

For the individual polymer samples, sample preparation was done by a CEF autosampler, at 1 mg/ml in ODCB, and dissolved at 160° C., for two hours, unless otherwise stated.

For the polymer blends, in order to ensure an accurate mixing ratio, as stated here, a required amount of two polymer samples were added to a two ounce, glass bottle. The polymer sample was dissolved in ODCB, at 160° C., under gentle stirring for two hours, with a Pierce Reacti-Therm III Heating/Stirring module (PO Box 114, Rockford, Ill. 61105, USA). The sample solution was quickly poured directly into a 10 ml glass vial at 150° C. The vial was then capped with a crimper. A "90 minute" dissolution time at 160° C. was used to dissolve the blend solution for HT-TGIC analysis Method to Test the Existence of Interaction Between the Inventive Substrates and Polymers Overview Polyethylene homopolymer (EO-1 sample) was used in this test. Instead of a typical HT-TGIC method, an isothermal process was used during the typical cooling process in HT-TGIC. The test consisted of the following steps.

Figure 2:
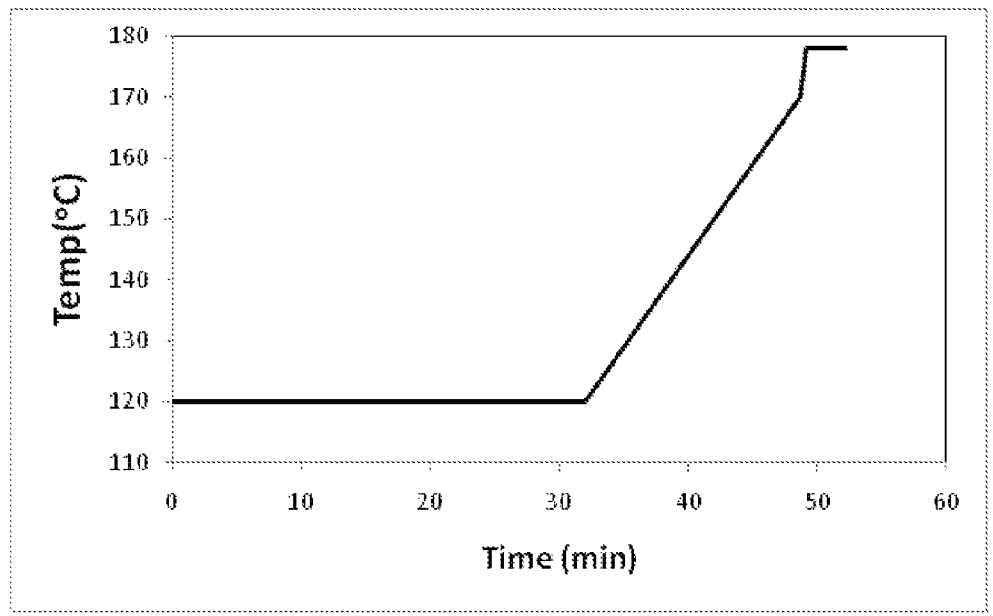
FIG. 2 depicts the "temperature versus time" profile for the isothermal HT-TGIC experiment, used to detect the interaction of the stationary phase with polyethylene homopolymer (EO-1) from solution at a specified temperature. The isothermal method at 120° C. is shown as an example.

EO-1 sample, at 1 mg/ml, was loaded onto the column at a specified temperature. A slow flow of ODCB, at 0.15 mL/min, was used to push the sample solution down the column, while keeping the column temperature unchanged for 20 minutes. If there was no interaction between EO-1 in solution and the stationary phase, as indicated by the generated chromatogram (for example, see FIG. 3), at this specified temperature, polymer fractions were eluted from the column The sample was eluted from the column by raising temperature from the specified isothermal temperature at 3° C./min, up to 178° C., with a solvent flow rate of 1.0 mL/min The chromatogram was recorded during elution. The retention volume, in milliliters, is defined as the amount of eluent used during the elution period. The "temperature versus time" profile is shown in FIG. 2, and the experimental parameters at isothermal temperature of 120° C. are listed in Table 4. The column(s) is/are contained in an oven, and the temperature of the oven is recorded.

The "temperature versus time" profile for the isothermal process at 120° C. (see FIG. 2) was used to detect the interaction of the stationary phase with polyethylene homopolymer (EO-1) from solution at a specified temperature.

Table 4 lists other experimental parameters (in addition to the description of FIG. 2) for testing the interaction between stationary phase and polyethylene homopolymer EO-1, in solution, by using an isothermal temperature of 120° C. instead of a cooling process.

TABLE 4

Experimental Parameters

| Temperature profile | | Column loading and vial filling | |
|---|---|---|---|
| Stabilization Temperature | 120° C. | Column Load Volume | 0.4 mL |
| Stabilization Rate | 10° C./min | Solvent pick up flow rate | 25 ml/min |
| Stabilization Time (Pre) | 5 min | Vial filling flow rate | 5 ml/min |
| Stabilization Time (Post) | 2 min | | |
| Crystallization Temperature | 120° C. | Loop Loading and filter cleaning | |
| Crystallization Rate | 10° C./min | Sample pick up flow rate | 2 ml/min |
| Crystallization Time | 20 min | Sample pick up volume | 2.2 ml |
| SF Time | 5 min | Load Loop Flow Rate | 1.25 mL/min |
| Elution Temperature | 170° C. | Load Loop Volume | 1.2 mL |
| Elution Rate | 3° C./min | Clean Line Flow Rate | 1.25 mL/min |
| Cleaning Temperature | 178° C. | Clean Line Volume | 4 mL |
| Cleaning Rate | 15° C./min | Clean Filter Flow Rate | 4 mL/min |
| Cleaning Time | 3 min | Clean Filter Volume | 5 mL |
| | | Cleaning Transfer Line Flow Rate | 5 mL/min |
| Temperature Zones | | Cleaning Transfer Line Volume | 2.00 ml |
| Top Oven Temperature | 150° C. | | |
| Transfer Line Temp | 150° C. | Pump flow | |
| Needle Temp | 150° C. | Pump Stabilization Time | 15 s |
| | | Cleaning Column Pump Flow | 1 mL/min |
| Dissolution | | Crystallization Pump Flow | 0.15 mL/min |
| Dissolution Temperature | 160° C. | Elution Pump Flow | 1 mL/min |
| Dissolution Stirring | 2 | Load Column Pump Flow | 0.3 mL/min |
| Dissolution time | 2 hours | | |

Results

Figure 3:
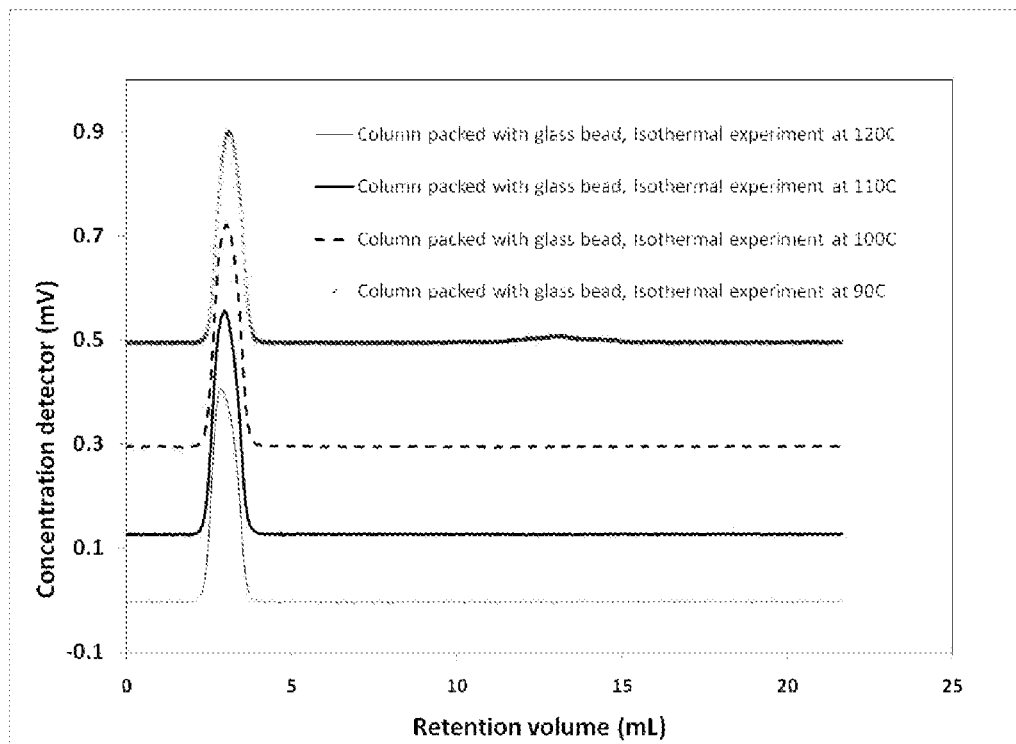
FIG. 3 depicts a series of HT-TGIC chromatograms obtained with different isothermal temperatures for the EO-1 polymer, using a comparative column packed with glass beads (an absence of interaction between the polymer in solution and glass beads).
Figure 4:
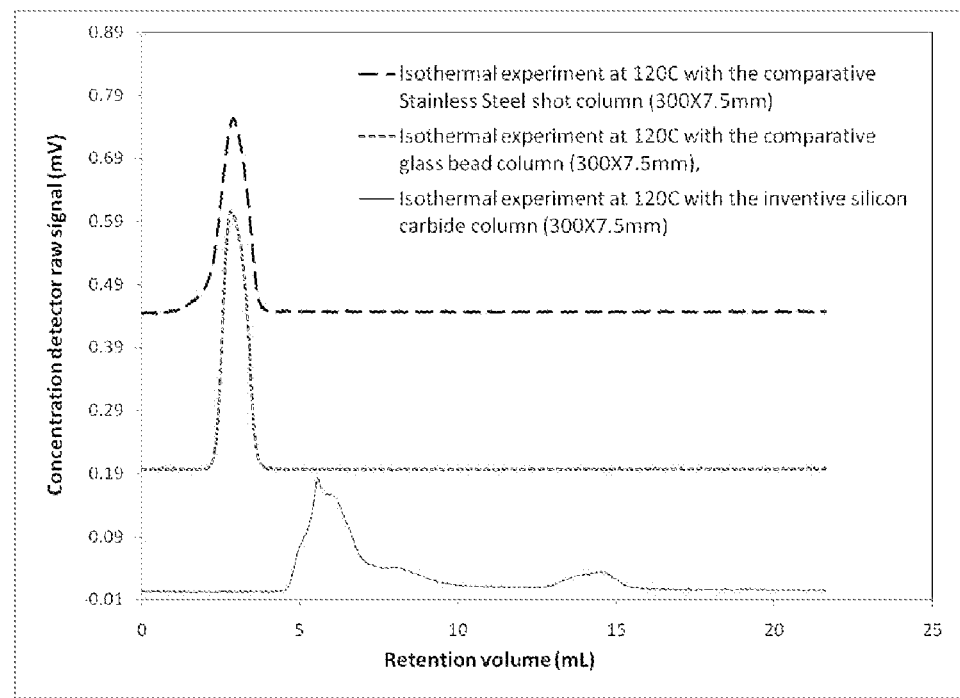
FIG. 4 depicts HT-TGIC chromatograms of the following: a) EO-1 polymer using the column packed with the silicon carbide (lowest profile)(the presence of the interaction between EO-1 in solution and substrate), b) EO-1 polymer using the column packed with glass beads (middle profile), and c) EO-1 polymer using the column packed with stainless steel shot (upper profile) (Another example for the absence of the interaction between EO-1 in solution and substrate).

FIG. 3 shows the EO-1 chromatograms obtained with the comparative column (glass beads) at 120° C., 110° C., 100° C. and 90° C. There is only one single symmetrical peak, indicating the absence of the interaction between EO-1 solution and glass beads, when the solution temperature is ≥100° C. When EO-1, a polyethylene homopolymer, is kept at a temperature of 90° C., a small amount of material crystallizes out of solution that elutes at a longer retention volume of 13 mL. The comparative stainless steel shot column is known to have no interactions with EO-1 in ODCB, when the solution temperature is ≥100° C. The results are significantly similar to the results obtained with the comparative glass bead column at the same experimental condition. As an example, the chromatogram of EO-1 with the comparative stainless steel column (300×7.5 mm) is shown in FIG. 4. The inventive silicon carbide column (dimension 300×7 5 mm) and the comparative glass bead column are tested at isothermal temperature of 120° C., 110° C., 100° C. and 90° C. with EO-1.

FIG. 4 also shows the chromatogram of EO-1 obtained with the inventive silicon carbide column (dimension 300×7 5 mm), together with the comparative stainless steel shot column (300×7.5 mm) and the comparative glass bead column (300×7 5 mm), all at 120° C. With the inventive silicon carbide column, the peak is neither a symmetric, nor a single peak. The peak appears at a much larger elution volume compared with the respective "EO-1 chromatograms" obtained with the comparative glass bead column and the comparative stainless steel column, each at same experimental condition. This difference clearly shows that there is interaction of EO-1, in solution, with the inventive packing material. Existence of the interaction may induce crystallization of EO-1 from solution onto the stationary phase. Existence of the interaction may also enhance the anchoring of EO-1 from solution to the stationary phase.

HT-TGIC Chromatograms Obtained with the Inventive Silicon Carbide Column (Dimension 300×7.5 mm)

Figure 5:
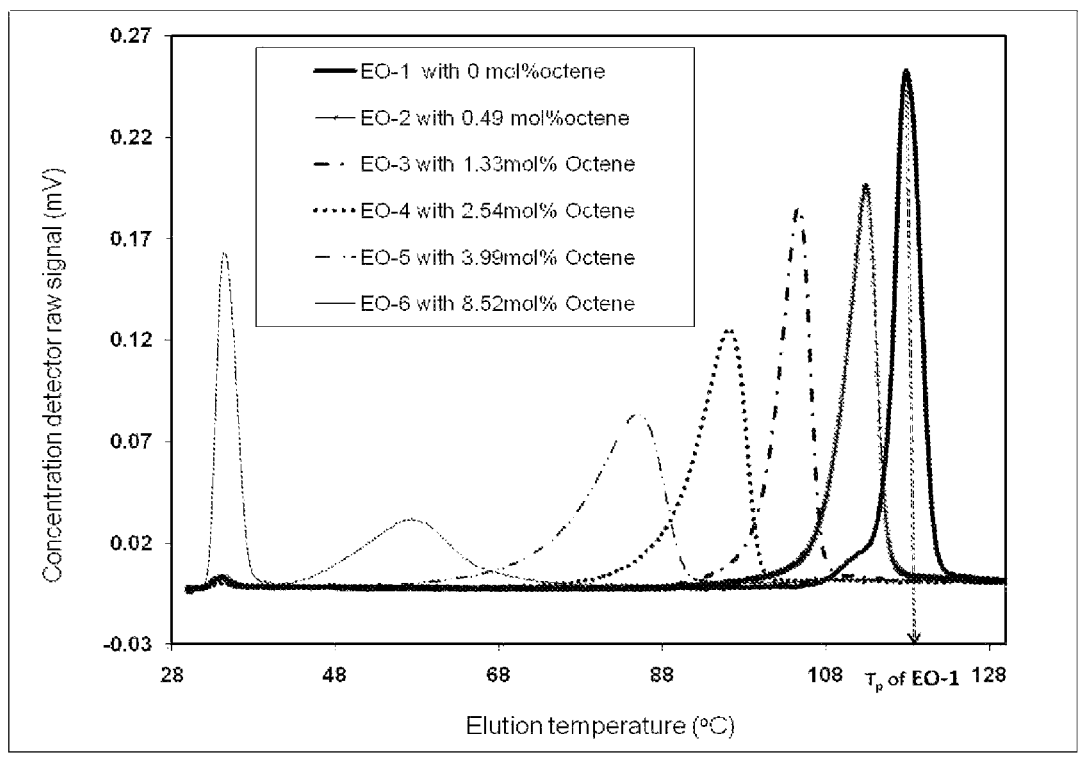
FIG. 5 depicts a series of HT-TGIC chromatograms of polymers EO-1 to EO-6, respectively, using an inventive silicon carbide column, and using the experimental parameters shown in Table 2.

Various EO materials were analyzed with the column packed with inventive packing material, using the column temperature profile shown in FIG. 1, and the experimental parameters listed in Table 2. The chromatograms of EO-1 to EO-6 are shown in FIG. 5. The elution temperature increased with the decrease in octene content. This indicates that the inventive silicon carbide column is capable of separating olefins-based polymers based on comonomer content.

EO-1 and EO-6 were analyzed using the comparative glass bead column (dimension 300×7.5 mm) with the same experimental conditions. The elution peak temperature is defined as the temperature of the oven (where the column is located) at the highest peak height of HT-TGIC chromatogram. The elution peak temperature of the inventive silicon carbide column (dimension 300×7.5 mm) is at 117.8° C. (EO-1). The elution peak temperature of the comparative glass bead column (dimension 300×7.5 mm) is 107.4 C (EO-1). The peak temperature of EO-1 with the inventive column shifts 10.4° C. to a higher temperature (see Table 5). Table 5 lists the shift in elution peak temperatures of several inventive apparatus (relative to a comparative column).

TABLE 5

Peak Elution Temperature of EO-1 by HT-TGIC

|  | Tp of EO-1 (° C.) | The shift of the peak temperature of EO-1 to a higher elution temperature (° C.) | Experimental condition |
|---|---|---|---|
| Inventive silicon carbide column (dimension 300 mm × 7.5 mm) | 117.8 | 11.4 | Listed in Table 2 |
| Comparative glass bead column (dimension 300 mm × 7.5 mm) | 107.4 | 0.00 | Same as above |
| Comparative stainless steel shot column (dimension 300 mmm × 7.5 mm) | 107.4 | 0.00 | Same as above |
| Inventive molybdenum sulfide column (dimension 50 mm × 7.5 mm) | 132.4 | 32.4 | Listed in Table 2 except 140° C._100° C._178° C._3° C./min_0.67° C./min_0.04 mL/min_0.3 mL/min |
| Comparative glass bead column (dimension 50 mm × 7.5 mm) | 100.0 | 0.00 | Same as above |
| Inventive mixed tungsten sulfide/glass column (dimension 50 mm × 7.5 mm) | 143.1 | 33.5 | Listed in Table 2 except TGIC140° C._30° C._178° C._3° C./min_3° C./min_0.01 mL/min_0.5 mL/min |
| Comparative glass bead column (dimension 50 mm × 7.5 mm) | 109.6 | 0.00 | Same as above |
| Inventive boron nitride column (50 mm × 7.5 mm) | 139.1 | 31.7 | Listed in Table 2 except TGIC150° C._30° C._178° C._3° C./min_3° C./min_0.02 mL/min_0.5 mL/min. |
| Comparative glass bead column (50 mm × 7.5 mm) | 109.6 | 0.00 | Listed in Table 2 except TGIC140° C._30° C._178° C._3° C./min_3° C./min_0.01 mL/min_0.5 mL/min |

Figure 6:
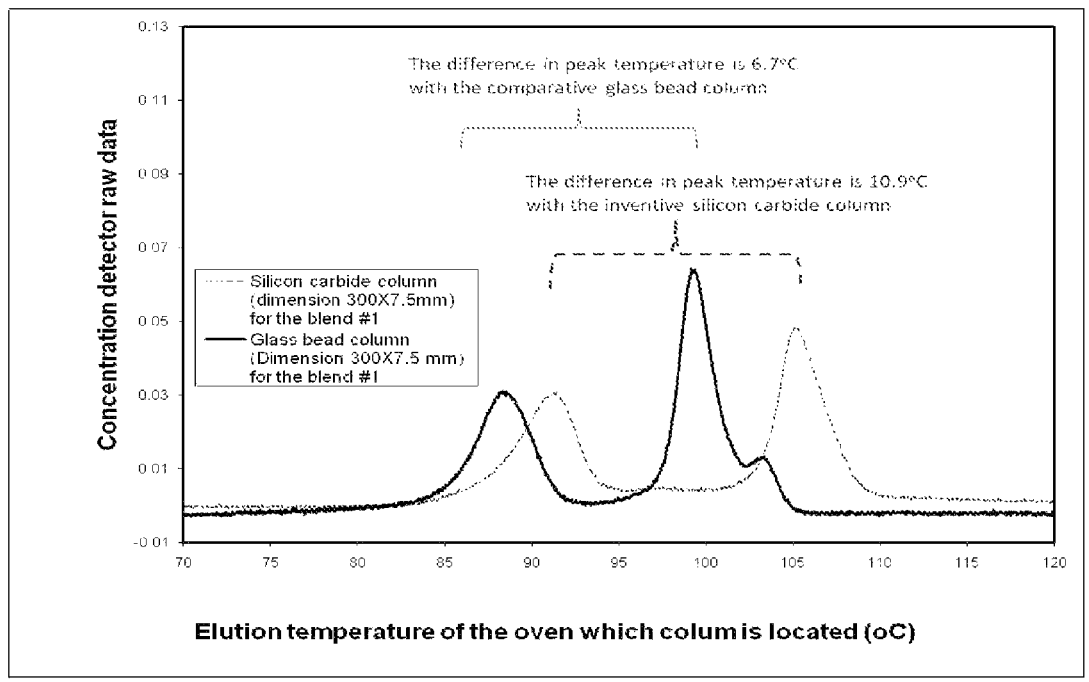
FIG. 6 depicts two HT-TGIC chromatograms of the Blend#1, using a comparative glass bead column (dimension 300 (L)×7.5 mm (ID)), as shown in the solid line profile, and an inventive silicon carbide column (dimension 300 (L)×7.5 mm (ID)), as shown in the dashed line profile. The "L" refers to the length of the column (in mm), and the "ID" refers to the internal diameter of the column.

An increase in the resolution of the inventive silicon carbide column, as compared to the comparative glass bead column, at the same chromatography conditions, is further demonstrated by using blend #1 as an example. Blend #1 is a solution blend of EO-3 and EO-7 at 50:50 (wt:wt) mixing ratio. FIG. 6 shows the respective HT-TGIC chromatograms of the Blend #1, using the inventive silicon carbide column and the comparative glass bead column. The comparative stainless steel column (300×7.5 mm) has substantially similar results as the comparative glass bead column (300×7.5 mm), thus the result is not shown in FIG. 6. It is clearly shown that a much better separation of the Blend #1 is obtained with the inventive silicon carbide column with a "closer to baseline" separation two peaks. With the comparative glass bead column, the difference in the peak temperature between the two peaks of Blend #1 is 6.7° C. With the inventive silicon carbide column, the difference in the peak temperature of Blend #1 is 10.9° C., which is 62.7% increase, compared to the comparative glass bead column Resolution here is defined as the difference in the elution peak temperature of two peaks of the Blend #1 divided by the sum of the half widths of the two peaks, where half width of each peak is defined as the peak width at the half height of the respective elution peak. Similar definition can be found in the following reference (Striegel, Yau, et al., *Modern Sice Exclusion Liquid Chromatography*, Wiley, the $2^{nd}$ edition, Page 42). For the comparative column, the half widths of the two peaks in Blend #1 are 3.891° C. and 2.503° C., respectively, and thus the resolution is calculated as "6.7/(3.891+2.503)=1.05." For the inventive column, the half widths of two peaks in Blend#1 are 4.089° C. and 3.340° C., respectively, and the resolution is calculated as "10.9/(4.089+3.34)=1.47." Therefore, the inventive column has an improved resolution by 40% ((1.47−1.05/1.05)× 100%=40%).

In addition, due to the existence of cocrystallization, when using the comparative glass bead column, in crystallization based techniques, there is an extra undesired shoulder at the high temperature peak area (FIG. 6). When discussing comonomer distribution analysis, co-crystallization refers to the phenomena that different chains with similar comonomer composition form crystals together" Co-crystallization is one of the key factors limiting the resolution of crystallization-based techniques. It is also very challenging to quantify the degree of cocrystallization. Because of this problem of co-crystallization, modeling or deconvolution of CRYSTAF, TREF and CEF chromatograms, for multi component systems, have been found to be very difficult However, due to the interaction between polyolefin and silicon carbide substrate, there is no extra undesired shoulder at high temperature, indicating that the cocrystallization is minimized in HT-TGIC.

As discussed above, FIG. 6 is a HT-TGIC chromatograms of the Blend #1 obtained by using the comparative glass bead column (dimension 300×7 5 mm) and the inventive silicon carbide column (dimension 300×7.5 mm) Experimental parameters are listed in Table 2, with the following changes: the stabilization temperature of 130° C., the elution temperature 140° C., the cooling rate 1.00° C./min, the elution rate 1.00° C./min; and the pump flow during cooling 0.05 mL/min HT-TGIC Chromatograms Obtained with the Inventive Molybdenum Sulfide Column (Dimension 50×7.5 mm)

The EO-1 and the Blend #1 were analyzed by HT-TGIC with the inventive molybdenum sulfide column (dimension 50 mm×7.5 mm) and the comparative glass bead column (dimension 50×7.5 mm) The experimental parameters were the same, as shown in Table 2, except for the following: the loading temperature 140° C., the cooling temperature 100°

C., the elution temperature 178° C., the cooling rate 3° C./min, the heating rate 0.67° C./min, the flow rate during cooling 0.04 mL/min, and the solvent flow rate during elution 0.3 mL/min FIG. 7 shows overlaid chromatograms of EO-1 and the Blend #1, each eluted from the molybdenum sulfide column. The peak temperature of EO-1 is 132.4° C. At 100° C., it is known that EO-1 does not interact with glass beads (see FIG. 3), and therefore EO-1 elutes at 100° C. In FIG. 7, the peak at the higher temperature of the Blend #1 overlays well with EO-1, since Blend #1 is 50:50 (wt:wt) solution blend of EO-3 and EO-7. Sample EO-7 has 0 mol % octene, which is the same as EO-1. This result indicates that the inventive molybdenum sulfide column is also capable of separating polyolefin based on comonomer content.

HT-TGIC with the Inventive Packing Material of Tungsten Sulfide and Glass Bead (1:2 wt:wt)

A mixture of tungsten sulfide with glass beads, at mixing ratio of 1:2 (wt:wt), was packed with slurry packing method at a column dimension 50 mm×7.5 mm The experimental parameters were the same as those listed in Table 2, except for the following: the final elution temperature 178° C., the flow rate during cooling 0.01 mL/min, the solvent flow rate during elution process 0.5 mL/min, and the sample concentration 0.15 mg/mL. Samples EO-1 to EO-6 were analyzed. The peak temperature increases with the decrease of octene content, and EO-1, with 0 mol % octene content, elutes at the higher temperature of 143.1° C. The elution peak temperature of the comparative glass beads at the same experimental conditions elutes at 109.6° C. The shift in the peak temperature of EO-1 is due to the existence of the interaction between tungsten sulfide and EO-1.

HT-TGIC with the Inventive Packing Material of Boron Nitride

Boron nitride was packed with the slurry packing method, using a column of dimension of 50 mm×7.5 mm The experimental parameters were the same as listed in Table 2, except with the following changes: the stabilization temperature 150° C., the elution temperature 178° C., the flow rate during cooling 0.02 mL/min, the flow rate during elution process 0.5 mL/min, and the sample concentration 0.5 mg/mL. Sample EO-1 was analyzed. The peak temperature was 139.1° C. The elution peak temperature of the comparative glass beads, at the same experimental conditions (except for the comparative column, the stabilization temperature was set at 140° C., and the flow rate during cooling was 0.01 mL/min) However, these minor differences in the two experimental parameters give basically same peak temperature for EO-1 as 109.4° C. (for comparative column). There is approximately a "31.4° C. temperature shift" in peak temperature to a high temperature. The shift in the peak temperature of EO-1 is due to the existence of the interaction between boron nitride and EO-1.

Improvement in Resolution Using Inventive Silicon Carbide Compared to Graphite

Figure 8:
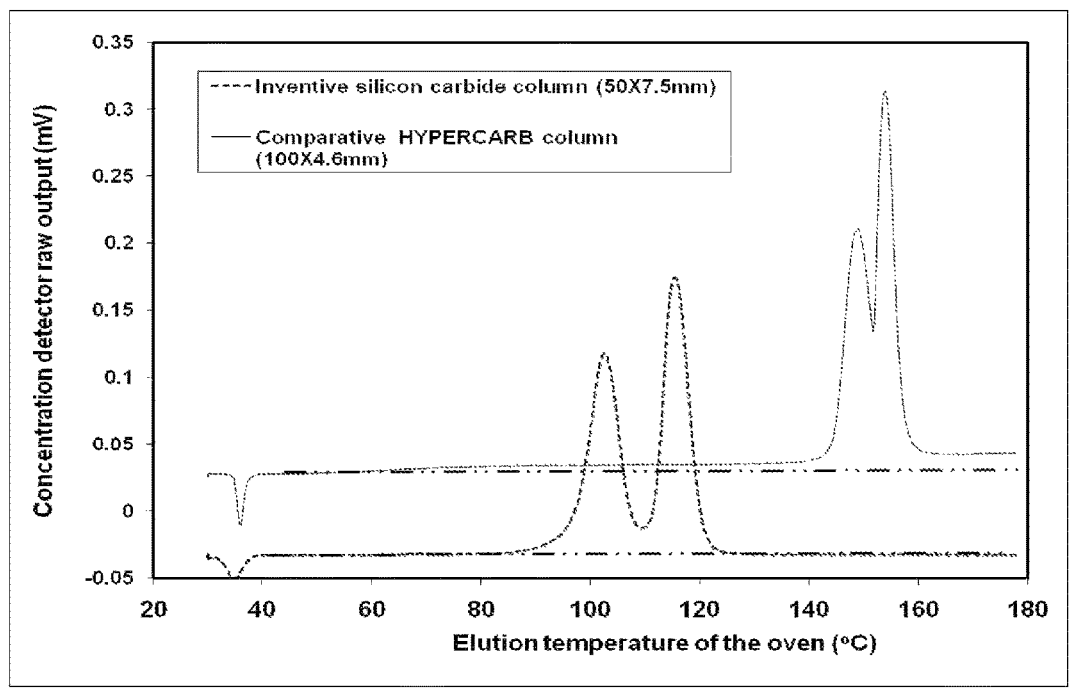
FIG. 8 depicts two HT-TGIC chromatograms of the Blend#1 using a comparative HYPERCARB column (dimension 100 (L)×4.6 mm (ID); upper profile) and an inventive silicon carbide column (dimension 100 (L)×7.5 mm (ID); lower profile).

Graphite is reported as an effective substrate for HT-LC (both solvent gradient and thermal gradient) (see Van Damme, et al. US 20100093964 A1, and Cong et al., Macromolecules, 2011, 44 (8), 3062-3072). The comparative column is HYPERCARB (dimension 100 mm×4.6 mm, Product number 35005-104646, lot PGC416). FIG. 8 shows the respective HT-TGIC chromatograms of Blend #1, obtained by using the comparative HYPERCARB column (dimension 100×4 6 mm) and the inventive silicon carbide column (dimension 100×7.5 mm). Experimental parameters are listed in Table 2 with the following changes: the stabilization temperature of 150° C., the elution temperature 178° C., the pump flow during cooling 0.02 mL/min, and the flow rate during elution 0.5 mL/min. The two peaks obtained with the silicon carbide are close to a baseline separation, while the peaks obtained with the comparative HYPERCARB column having significant overlap. This indicates that the silicon carbide leads to an increased resolution, as compared to the graphite. Also, as seen in FIG. 8, a dotted line was added to each chromatograph for a better visualization of baseline drift. This indication of baseline drift clearly shows that the two components of Blend #1 are better separated, with a flatter baseline, when using the inventive silicon carbide as the stationary phase, compared to the use of the graphite as the stationary phase.

The invention claimed is:

1. A method for HT-TGIC polymer chromatography to separate an olefin-based polymer with a density from 0.83 g/cc to 0.97 g/cc, based on comonomer content, said method comprising introducing a solution, comprising a polymer, into a liquid flowing through a first stationary phase,
    wherein the first stationary phase comprises molybdenum sulfide ($MoS_2$) with a particle size from 10 to 30 μm; and
    wherein the polymer is an olefin-based polymer that has a density from 0.83 g/cc to 0.97 g/cc; and
    wherein the method comprises (1) dissolving the polymer to form a sample solution, (2) loading the sample solution onto a column, (3) cooling the column, such that polymer fractions of the polymer are anchored onto the first stationary phase of column, and (4) eluting the polymer fractions, and measuring the concentration of the polymer fractions; and
    wherein the stationary phase is subject to the following temperature profile: from 140° C. to 30° C., and then to 150° C.

2. The method of claim 1, wherein the first stationary phase comprises an atomically flat crystalline composition comprising at least two different atoms.

3. The method of claim 1, wherein the first stationary phase further comprises an inert filler.

4. The method of claim 3, wherein the compound is chemically bonded to the inert filler.

5. The method of claim 3, wherein the compound is coated onto the inert filler.

* * * * *